(12) United States Patent  
Walter et al.

(10) Patent No.: US 7,687,744 B2  
(45) Date of Patent: Mar. 30, 2010

(54) COORDINATED EMISSION OF FRAGRANCE, LIGHT, AND SOUND

(75) Inventors: Scott D. Walter, Twin Lakes, WI (US); Jeffrey J. Wolf, Racine, WI (US); Jose Porchia, Greenfield, WI (US); David A. Tomkins, Racine, WI (US); Thomas A. Helf, New Berlin, WI (US); James R. Crapser, Racine, WI (US); Kelley H. Rich, Libertyville, IL (US); Barry T. Calpino, Park Ridge, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/514,295

(22) PCT Filed: May 13, 2003

(86) PCT No.: PCT/US03/14769

§ 371 (c)(1),  
(2), (4) Date: Apr. 22, 2005

(87) PCT Pub. No.: WO03/098971

PCT Pub. Date: Nov. 27, 2003

(65) Prior Publication Data

US 2005/0185392 A1 Aug. 25, 2005

(51) Int. Cl.  
*H05B 1/02* (2006.01)

(52) U.S. Cl. ............... 219/505; 219/506; 219/502; 219/494; 392/390; 422/122; 422/125

(58) Field of Classification Search ............... 219/494, 219/497, 499, 501, 505, 506, 438, 386, 507–509, 219/492, 526, 502; 392/390  
See application file for complete search history.

(56) References Cited

U.S. PATENT DOCUMENTS 38,150 A 4/1863 Colburn (Continued)

FOREIGN PATENT DOCUMENTS

DE 3609511 10/1986

(Continued)

OTHER PUBLICATIONS

European Search Report Appl. No. EP 04709400.8 dated Oct. 4, 2006.

(Continued)

*Primary Examiner*—Mark H Paschall

(57) ABSTRACT

A novel apparatus for producing combined presentation of light and aroma to produce a desired overall sensory effect. The includes a fragrance dispenser (31), a light source (42), an audio system (52), and a microprocessor (99). The fragrance dispenser (31) is refillable and controllable, so as to adjust the rate at which the fragrance dispenser dispenses a fragrance. The light source (42) comprises a plurality of LEDs (40a-40c) of at least two different colors and is controllable so as to adjust the operation of the plurality of LEDs (40a-40c). The audio system (52) controls sounds to be emitted from the apparatus. The microprocessor (99) controls the rate at which the fragrance dispenser (31) dispenses fragrance and the operation of the light source (42) and audio system (52).

46 Claims, 12 Drawing Sheets

U.S. PATENT DOCUMENTS

| | | |
|---|---|---|
| 446,953 A | 2/1891 | Robert |
| 514,422 A | 2/1894 | Kellogg |
| 554,115 A | 2/1896 | Fisher |
| 699,652 A | 5/1902 | Campbell et al. |
| 1,178,575 A | 4/1916 | Collins |
| 1,403,548 A | 1/1922 | Gudeman |
| 1,712,204 A | 5/1929 | Gibney |
| 1,751,257 A | 3/1930 | Vallebuona et al. |
| 1,800,156 A | 4/1931 | Rotheim |
| 1,977,997 A | 10/1934 | Patterson et al. |
| 1,981,650 A | 11/1934 | Larsen |
| 1,994,932 A | 3/1935 | Vidal |
| 2,192,019 A | 2/1940 | Schepmoes |
| 2,230,265 A | 2/1941 | Robinson |
| 2,372,371 A | 3/1945 | Eisner |
| 2,412,128 A | 12/1946 | Coyle |
| 2,424,268 A | 7/1947 | Delane et al. |
| 2,435,756 A | 2/1948 | Schlesinger |
| 2,469,656 A | 5/1949 | Lienert |
| 2,557,501 A | 6/1951 | Fusay et al. |
| 2,591,818 A | 4/1952 | Huff |
| 2,597,195 A | 5/1952 | Smith |
| 2,668,993 A | 2/1954 | Bair |
| 2,931,880 A | 4/1960 | Yaffe |
| 2,942,090 A | 6/1960 | Diehl |
| 3,248,530 A | 4/1966 | Titmas |
| 3,358,552 A | 12/1967 | Schneider |
| 3,373,341 A | 3/1968 | Wattson |
| 3,386,005 A | 5/1968 | Roland et al. |
| 3,436,310 A | 4/1969 | Arnold et al. |
| 3,443,083 A | 5/1969 | Curran |
| 3,543,122 A | 11/1970 | Klebanoff et al. |
| 3,545,650 A | 12/1970 | Williams |
| 3,588,859 A | 6/1971 | Petree |
| 3,615,041 A | 10/1971 | Bischoff |
| 3,747,902 A | 7/1973 | Bailey |
| 3,780,260 A | 12/1973 | Elsner |
| 3,790,772 A | 2/1974 | Newman et al. |
| 3,864,080 A | 2/1975 | Valbona et al. |
| 3,872,280 A | 3/1975 | Van Dalen |
| 3,948,445 A | 4/1976 | Andeweg |
| 4,084,079 A | 4/1978 | Costello |
| 4,106,671 A | 8/1978 | Sharples |
| 4,166,293 A | 9/1979 | Anis |
| 4,184,612 A | 1/1980 | Freyre |
| 4,197,671 A | 4/1980 | De Brouwer |
| 4,202,387 A | 5/1980 | Upton |
| 4,217,315 A | 8/1980 | Keeler, II |
| 4,229,415 A | 10/1980 | Bryson |
| 4,244,525 A | 1/1981 | Manna |
| 4,250,537 A | 2/1981 | Roegner et al. |
| 4,285,028 A | 8/1981 | Sundin et al. |
| 4,301,095 A | 11/1981 | Mettler et al. |
| 4,315,665 A | 2/1982 | Haines |
| 4,338,547 A | 7/1982 | McCaslin |
| 4,346,059 A | 8/1982 | Spector |
| 4,391,781 A | 7/1983 | van Lit |
| 4,415,797 A | 11/1983 | Choustoulakis |
| 4,432,938 A | 2/1984 | Meetze, Jr. |
| 4,435,732 A | 3/1984 | Hyatt |
| 4,493,011 A | 1/1985 | Spector |
| 4,549,250 A | 10/1985 | Spector |
| 4,571,485 A | 2/1986 | Spector |
| 4,583,686 A | 4/1986 | Martens et al. |
| 4,597,781 A | 7/1986 | Spector |
| 4,609,978 A | 9/1986 | Hsieh et al. |
| 4,611,266 A | 9/1986 | Schwartz |
| 4,666,638 A | 5/1987 | Baker et al. |
| 4,670,820 A | 6/1987 | Eddins et al. |
| 4,675,575 A | 6/1987 | Smith et al. |
| 4,689,515 A | 8/1987 | Benndorf et al. |
| 4,695,435 A | 9/1987 | Spector |
| 4,702,418 A * | 10/1987 | Carter et al. ................ 239/101 |
| 4,703,155 A | 10/1987 | Suhajda |
| 4,703,314 A | 10/1987 | Spani |
| 4,707,338 A | 11/1987 | Spector |
| 4,714,984 A | 12/1987 | Spector |
| 4,715,702 A | 12/1987 | Dillon |
| 4,739,928 A | 4/1988 | O'Neil |
| 4,750,471 A | 6/1988 | Hautmann et al. |
| 4,785,642 A | 11/1988 | Chin et al. |
| 4,795,883 A | 1/1989 | Glucksman et al. |
| 4,816,973 A | 3/1989 | Atalla et al. |
| 4,830,791 A | 5/1989 | Muderlak et al. |
| 4,837,421 A | 6/1989 | Luthy |
| 4,840,444 A | 6/1989 | Hewitt |
| 4,844,050 A | 7/1989 | Hautmann et al. |
| 4,849,606 A | 7/1989 | Martens, III et al. |
| 4,856,103 A | 8/1989 | Compton |
| 4,858,079 A | 8/1989 | Ohashi |
| 4,866,580 A | 9/1989 | Blackerby |
| 4,870,551 A | 9/1989 | Nagel |
| 4,873,029 A | 10/1989 | Blum |
| 4,934,792 A | 6/1990 | Tovi |
| 4,955,714 A | 9/1990 | Stotler et al. |
| 4,968,487 A | 11/1990 | Yamamoto et al. |
| 5,017,909 A | 5/1991 | Goekler |
| 5,038,394 A | 8/1991 | Hawegawa et al. |
| 5,055,822 A | 10/1991 | Campbell et al. |
| 5,095,647 A | 3/1992 | Zobele et al. |
| 5,111,477 A | 5/1992 | Muderlak et al. |
| 5,115,975 A | 5/1992 | Shilling |
| 5,118,319 A | 6/1992 | Smith et al. |
| 5,135,485 A | 8/1992 | Cohen et al. |
| 5,136,483 A | 8/1992 | Schoniger et al. |
| 5,147,585 A | 9/1992 | Blum |
| 5,175,791 A * | 12/1992 | Muderlak et al. ........... 392/390 |
| 5,192,342 A | 3/1993 | Baron et al. |
| 5,201,025 A | 4/1993 | Landesberg |
| 5,212,672 A | 5/1993 | Loisch et al. |
| 5,213,523 A | 5/1993 | Hygema et al. |
| 5,214,458 A | 5/1993 | Kanai |
| 5,222,186 A | 6/1993 | Schimanski et al. |
| 5,230,837 A | 7/1993 | Babasade |
| 5,231,266 A * | 7/1993 | Warren ....................... 219/521 |
| 5,233,375 A | 8/1993 | Williams et al. |
| 5,233,680 A | 8/1993 | Fussell |
| 5,260,919 A | 11/1993 | Tsai |
| 5,274,215 A | 12/1993 | Jackson |
| 5,283,601 A | 2/1994 | Lowe |
| 5,283,723 A | 2/1994 | Wu |
| 5,296,681 A | 3/1994 | Tschauder |
| 5,309,185 A | 5/1994 | Harper |
| 5,309,338 A | 5/1994 | Liu |
| 5,324,490 A | 6/1994 | Van Vlahakis |
| D350,209 S | 8/1994 | Martin |
| 5,370,829 A | 12/1994 | Kunze |
| 5,382,410 A | 1/1995 | Peltier |
| 5,392,379 A | 2/1995 | Fussell |
| D357,330 S | 4/1995 | Wong et al. |
| 5,416,228 A | 5/1995 | Ewen et al. |
| 5,419,879 A | 5/1995 | Vlahakis et al. |
| 5,432,623 A | 7/1995 | Egan et al. |
| 5,449,117 A | 9/1995 | Muderlak et al. |
| 5,452,270 A | 9/1995 | Ikeda et al. |
| 5,455,750 A | 10/1995 | Davis et al. |
| 5,464,710 A | 11/1995 | Yang |
| 5,483,689 A | 1/1996 | O'Donnell, Jr. et al. |
| 5,484,086 A | 1/1996 | Pu |
| 5,485,308 A | 1/1996 | Hirata et al. |
| 5,497,102 A | 3/1996 | Burrows et al. |
| 5,498,397 A | 3/1996 | Horng |
| 5,512,371 A | 4/1996 | Gupta et al. |
| 5,517,264 A | 5/1996 | Sutton |

| | | | | | | |
|---|---|---|---|---|---|---|
| 5,521,357 A | 5/1996 | Lock et al. | | D437,069 S | 1/2001 | Allison |
| 5,524,101 A | 6/1996 | Thorgersen et al. | | D437,636 S | 2/2001 | Basaganas |
| D372,769 S | 8/1996 | Ganor | | 6,191,826 B1 | 2/2001 | Murakami et al. |
| 5,544,812 A | 8/1996 | Torres | | 6,196,471 B1 | 3/2001 | Ruthenberg |
| 5,549,247 A | 8/1996 | Rossman et al. | | 6,199,983 B1 | 3/2001 | Kato et al. |
| 5,556,192 A | 9/1996 | Wang | | 6,211,626 B1 | 4/2001 | Lys et al. |
| 5,591,409 A | 1/1997 | Watkins | | 6,216,925 B1 | 4/2001 | Garon |
| 5,616,172 A | 4/1997 | Tuckerman et al. | | 6,236,807 B1 | 5/2001 | Ruffolo et al. |
| 5,633,623 A | 5/1997 | Campman | | 6,239,216 B1 | 5/2001 | Montanari et al. |
| D381,443 S | 7/1997 | Yuen | | 6,241,362 B1 | 6/2001 | Morrison |
| D381,444 S | 7/1997 | Yuen | | 6,254,065 B1 | 7/2001 | Ehrensperger et al. |
| 5,647,052 A | 7/1997 | Patel et al. | | 6,267,297 B1 | 7/2001 | Contadini et al. |
| 5,647,053 A | 7/1997 | Schroeder et al. | | 6,268,062 B1 | 7/2001 | Demeuse |
| 5,662,835 A | 9/1997 | Collingwood | | 6,270,720 B1 | 8/2001 | Mandish |
| 5,673,825 A | 10/1997 | Chen | | 6,275,651 B1 | 8/2001 | Voit |
| 5,690,509 A | 11/1997 | Eisenbraun | | 6,278,840 B1 | 8/2001 | Basaganas Millan |
| D386,974 S | 12/1997 | Wefler | | 6,281,867 B2 | 8/2001 | Kurematsu |
| 5,716,119 A | 2/1998 | Patel | | 6,292,196 B1 | 9/2001 | Fukunaga et al. |
| D393,063 S | 3/1998 | Wefler | | 6,292,305 B1 | 9/2001 | Sakuma et al. |
| 5,734,590 A | 3/1998 | Tebbe | | 6,292,901 B1 | 9/2001 | Lys et al. |
| 5,747,940 A | 5/1998 | Openiano | | 6,302,559 B1 | 10/2001 | Warren |
| 5,749,646 A | 5/1998 | Brittell | | 6,318,876 B1 | 11/2001 | Sigro et al. |
| 5,752,766 A | 5/1998 | Bailey et al. | | 6,337,080 B1 | 1/2002 | Fryan et al. |
| 5,757,111 A | 5/1998 | Sato | | 6,340,868 B1 | 1/2002 | Lys et al. |
| 5,757,459 A | 5/1998 | Bhalakia et al. | | 6,341,732 B1 | 1/2002 | Martin et al. |
| D395,529 S | 6/1998 | Yuen | | D453,562 S | 2/2002 | Makino |
| 5,763,080 A | 6/1998 | Stahl et al. | | 6,350,417 B1 | 2/2002 | Lau et al. |
| 5,772,074 A | 6/1998 | Dial et al. | | 6,361,752 B1 | 3/2002 | Demarest et al. |
| 5,788,931 A | 8/1998 | Munoz Quintana | | D455,486 S | 4/2002 | Makino |
| 5,830,578 A | 11/1998 | Ono et al. | | 6,368,564 B1 | 4/2002 | Smith |
| 5,852,946 A | 12/1998 | Cowger | | 6,377,164 B1 | 4/2002 | Fulmer |
| 5,853,672 A | 12/1998 | Lorman et al. | | D457,667 S | 5/2002 | Piepgras |
| 5,863,108 A | 1/1999 | Lederer | | D457,669 S | 5/2002 | Piepgras |
| 5,871,153 A | 2/1999 | Doggett, Jr. | | D457,974 S | 5/2002 | Piepgras |
| 5,875,968 A | 3/1999 | Miller et al. | | 6,390,453 B1 | 5/2002 | Frederickson et al. |
| 5,876,678 A | 3/1999 | Harrell et al. | | 6,392,549 B1 | 5/2002 | Wu |
| 5,903,710 A | 5/1999 | Wefler et al. | | D458,395 S | 6/2002 | Piepgras |
| 5,909,845 A | 6/1999 | Greatbatch et al. | | 6,398,381 B1 | 6/2002 | Tseng |
| 5,922,231 A | 7/1999 | Karst et al. | | D460,544 S | 7/2002 | Garcia |
| 5,924,784 A | 7/1999 | Chliwnyj et al. | | D460,573 S | 7/2002 | Gee, II |
| 5,926,614 A | 7/1999 | Steinel | | 6,420,877 B1 | 7/2002 | Replogle |
| D412,569 S | 8/1999 | Muller | | 6,423,892 B1 | 7/2002 | Ramaswamy |
| 5,937,140 A | 8/1999 | Leonard et al. | | D461,549 S | 8/2002 | Garcia |
| 5,940,577 A | 8/1999 | Steinel | | D461,885 S | 8/2002 | Jordi |
| 5,945,094 A | 8/1999 | Martin et al. | | 6,431,719 B1 | 8/2002 | Lau et al. |
| 5,964,519 A | 10/1999 | Chun-Ying | | 6,439,471 B2 | 8/2002 | Ehrlich et al. |
| 5,976,503 A | 11/1999 | Martin et al. | | D462,755 S | 9/2002 | Millan |
| 5,980,064 A | 11/1999 | Metroyanis | | D463,610 S | 9/2002 | Piepgras |
| 6,016,038 A * | 1/2000 | Mueller et al. ............... 315/291 | | 6,446,880 B1 | 9/2002 | Schram et al. |
| 6,020,983 A | 2/2000 | Neu et al. | | D464,416 S | 10/2002 | von Dohlen et al. |
| 6,039,899 A | 3/2000 | Martin et al. | | 6,457,826 B1 | 10/2002 | Lett |
| 6,044,202 A | 3/2000 | Junkel | | 6,459,919 B1 | 10/2002 | Lys et al. |
| 6,072,606 A | 6/2000 | Huether et al. | | 6,466,739 B2 | 10/2002 | Ambrosi et al. |
| 6,097,881 A | 8/2000 | DeWitt et al. | | 6,478,440 B1 | 11/2002 | Jaworski et al. |
| 6,101,038 A | 8/2000 | Hebert et al. | | 6,479,594 B1 | 11/2002 | Cheung et al. |
| 6,104,866 A | 8/2000 | DeWitt et al. | | 6,482,863 B2 | 11/2002 | Munagavalasa et al. |
| 6,104,867 A | 8/2000 | Stathakis et al. | | D468,033 S | 12/2002 | Warren et al. |
| 6,123,935 A | 9/2000 | Wefler et al. | | D468,035 S | 12/2002 | Blanc et al. |
| 6,135,369 A | 10/2000 | Prendergast et al. | | 6,503,459 B1 | 1/2003 | Leonard et al. |
| D433,521 S | 11/2000 | Jaworski | | D469,862 S | 2/2003 | Cruver, IV et al. |
| D433,744 S | 11/2000 | Basaganas | | 6,528,954 B1 | 3/2003 | Lys et al. |
| 6,142,653 A | 11/2000 | Larson | | 6,536,746 B2 | 3/2003 | Watkins |
| 6,145,241 A | 11/2000 | Okuno | | D473,638 S | 4/2003 | Cruver, IV |
| 6,149,283 A | 11/2000 | Conway et al. | | 6,547,553 B2 | 4/2003 | Koch et al. |
| 6,150,774 A | 11/2000 | Mueller et al. | | 6,548,967 B1 | 4/2003 | Dowling et al. |
| 6,150,943 A | 11/2000 | Lehman et al. | | 6,554,203 B2 | 4/2003 | Hess et al. |
| 6,151,827 A | 11/2000 | Smith et al. | | 6,557,998 B2 | 5/2003 | Portney |
| 6,153,703 A | 11/2000 | Lustiger et al. | | 6,558,022 B2 | 5/2003 | Kawahara |
| 6,154,607 A | 11/2000 | Flashinski et al. | | 6,567,613 B2 | 5/2003 | Rymer |
| D434,842 S | 12/2000 | Thomas et al. | | 6,568,659 B2 | 5/2003 | Hugon |
| 6,163,098 A | 12/2000 | Taylor et al. | | 6,569,387 B1 | 5/2003 | Furner et al. |
| 6,166,496 A | 12/2000 | Lys et al. | | D475,446 S | 6/2003 | Millan |
| D436,657 S | 1/2001 | Heatter | | 6,575,610 B2 | 6/2003 | Natsume |

| | | | |
|---|---|---|---|
| 6,577,080 B2 | 6/2003 | Lys et al. | |
| 6,581,915 B2 | 6/2003 | Bartsch et al. | |
| 6,584,986 B2 | 7/2003 | Gindl | |
| 6,588,435 B1 | 7/2003 | Gindl | |
| 6,602,475 B1 | 8/2003 | Chiao | |
| 6,603,924 B2 | 8/2003 | Brown et al. | |
| 6,606,548 B2 | 8/2003 | Kato et al. | |
| 6,608,453 B2 | 8/2003 | Morgan et al. | |
| 6,611,297 B1 | 8/2003 | Akashi et al. | |
| 6,619,559 B2 | 9/2003 | Wohrle et al. | |
| 6,622,662 B1 | 9/2003 | Wolpert et al. | |
| 6,624,597 B2 | 9/2003 | Dowling et al. | |
| D480,792 S | 10/2003 | Millan | |
| 6,631,888 B1 | 10/2003 | Prueter | |
| D481,787 S | 11/2003 | Millan | |
| 6,644,507 B2 | 11/2003 | Borut et al. | |
| D483,104 S | 12/2003 | Hill et al. | |
| 6,661,967 B2 | 12/2003 | Levine et al. | |
| 6,667,576 B1 | 12/2003 | Westhoff | |
| 6,676,284 B1 | 1/2004 | Wynne Willson | |
| 6,682,331 B1 | 1/2004 | Peh et al. | |
| 6,685,339 B2 | 2/2004 | Daughtry et al. | |
| 6,685,343 B2 | 2/2004 | Mabuchi | |
| 6,688,752 B2 | 2/2004 | Moore | |
| 6,690,120 B2 | 2/2004 | Oskorep et al. | |
| 6,697,571 B2 | 2/2004 | Triplett et al. | |
| 6,698,665 B2 | 3/2004 | Minamite et al. | |
| 6,713,024 B1 | 3/2004 | Arnell et al. | |
| 6,714,725 B2 | 3/2004 | Grone et al. | |
| 6,717,376 B2 | 4/2004 | Lys et al. | |
| 6,719,217 B1 | 4/2004 | Tawara et al. | |
| 6,720,745 B2 | 4/2004 | Lys et al. | |
| 6,721,102 B2 | 4/2004 | Bourdelais et al. | |
| 6,727,332 B2 | 4/2004 | Demain | |
| 6,729,552 B1 | 5/2004 | McEwen | |
| 6,729,746 B2 | 5/2004 | Suehiro et al. | |
| 6,733,719 B2 | 5/2004 | DiNardo et al. | |
| 6,733,898 B2 | 5/2004 | Kim et al. | |
| 6,741,351 B2 | 5/2004 | Marshall et al. | |
| D491,678 S | 6/2004 | Piepgras | |
| D492,042 S | 6/2004 | Piepgras | |
| 6,752,327 B2 | 6/2004 | Martens, III et al. | |
| 6,758,566 B2 | 7/2004 | Goulden et al. | |
| 6,759,961 B2 | 7/2004 | Fitzgerald et al. | |
| 6,763,624 B2 | 7/2004 | Gow | |
| 6,766,773 B2 | 7/2004 | Wolpert et al. | |
| 6,768,865 B2 | 7/2004 | Stathakis et al. | |
| 6,774,584 B2 | 8/2004 | Lys et al. | |
| 6,775,470 B2 | 8/2004 | Zobele et al. | |
| 6,777,891 B2 | 8/2004 | Lys et al. | |
| 6,779,905 B1 | 8/2004 | Mazursky et al. | |
| 6,781,329 B2 | 8/2004 | Mueller et al. | |
| 6,782,194 B2 | 8/2004 | Schneiderbauer | |
| 6,783,117 B2 | 8/2004 | Wohrle | |
| 6,788,011 B2 | 9/2004 | Mueller et al. | |
| 6,792,199 B2 | 9/2004 | Levine et al. | |
| 6,801,003 B2 | 10/2004 | Schanberger et al. | |
| 6,802,460 B2 | 10/2004 | Hess et al. | |
| 6,806,659 B1 | 10/2004 | Mueller et al. | |
| 6,810,204 B2 | 10/2004 | Grone et al. | |
| 6,811,287 B2 | 11/2004 | Roller et al. | |
| 6,813,094 B2 | 11/2004 | Kaminsky et al. | |
| 6,819,506 B1 | 11/2004 | Taylor et al. | |
| 6,824,296 B2 | 11/2004 | Souza et al. | |
| 6,827,286 B2 | 12/2004 | Zobele | |
| 6,827,466 B2 | 12/2004 | Tsai | |
| 6,829,852 B1 | 12/2004 | Uehran | |
| 6,832,794 B2 | 12/2004 | He et al. | |
| 6,837,585 B2 | 1/2005 | Roggatz | |
| 6,839,506 B2 | 1/2005 | He et al. | |
| 6,843,965 B2 | 1/2005 | Matulevich | |
| 6,843,969 B1 | 1/2005 | Anno | |
| 6,846,098 B2 | 1/2005 | Bourdelais et al. | |
| 6,848,795 B2 | 2/2005 | Kaminsky et al. | |
| 6,850,697 B2 | 2/2005 | Basaganas Millan | |
| 6,854,717 B2 | 2/2005 | Millan | |
| 6,857,579 B2 | 2/2005 | Harris | |
| D502,540 S | 3/2005 | Cruver, IV et al. | |
| 6,862,402 B2 | 3/2005 | Kim | |
| 6,864,110 B2 | 3/2005 | Summers et al. | |
| 6,869,204 B2 | 3/2005 | Morgan et al. | |
| 6,871,794 B2 | 3/2005 | McEwen | |
| 6,871,982 B2 | 3/2005 | Homan et al. | |
| D504,171 S | 4/2005 | Ibarra et al. | |
| 6,883,929 B2 | 4/2005 | Dowling | |
| 6,885,811 B2 | 4/2005 | He et al. | |
| 6,888,322 B2 | 5/2005 | Dowling et al. | |
| 6,889,003 B2 | 5/2005 | Triplett et al. | |
| 6,890,642 B2 | 5/2005 | Kaminsky et al. | |
| 6,895,177 B2 | 5/2005 | He et al. | |
| 6,897,381 B2 | 5/2005 | He et al. | |
| 6,897,624 B2 | 5/2005 | Lys et al. | |
| 6,899,280 B2 | 5/2005 | Kotary et al. | |
| 6,901,215 B2 | 5/2005 | He et al. | |
| 6,901,925 B2 | 6/2005 | Coughlin | |
| 6,909,840 B2 | 6/2005 | Harwig et al. | |
| 6,917,402 B2 | 7/2005 | Hosoda et al. | |
| 6,917,754 B2 | 7/2005 | Pedrotti et al. | |
| 6,920,282 B2 | 7/2005 | He et al. | |
| D508,558 S | 8/2005 | Wolpert et al. | |
| 6,923,383 B1 | 8/2005 | Joshi | |
| 6,924,233 B1 | 8/2005 | Chua et al. | |
| 6,926,435 B2 | 8/2005 | Li | |
| 6,931,202 B2 | 8/2005 | Pedrotti et al. | |
| 6,933,680 B2 | 8/2005 | Oskorep et al. | |
| 6,936,978 B2 | 8/2005 | Morgan et al. | |
| 6,938,883 B2 | 9/2005 | Adams et al. | |
| 6,945,468 B1 | 9/2005 | Rodriguez et al. | |
| 6,946,805 B2 | 9/2005 | Segan et al. | |
| 6,950,607 B2 | 9/2005 | Yip et al. | |
| 6,953,260 B1 | 10/2005 | Allen | |
| 6,953,265 B2 | 10/2005 | Suehiro et al. | |
| 6,955,581 B1 | 10/2005 | Liu | |
| 6,957,012 B2 | 10/2005 | He et al. | |
| 6,965,205 B2 | 11/2005 | Piepgras et al. | |
| 6,967,448 B2 | 11/2005 | Morgan et al. | |
| 6,969,954 B2 | 11/2005 | Lys | |
| 6,975,079 B2 | 12/2005 | Lys et al. | |
| 2001/0011779 A1 | 8/2001 | Stover | |
| 2001/0032655 A1 | 10/2001 | Gindi | |
| 2002/0009945 A1 | 1/2002 | Spector | |
| 2002/0021892 A1 | 2/2002 | Ambrosi et al. | |
| 2002/0036617 A1 | 3/2002 | Pryor | |
| 2002/0048169 A1 | 4/2002 | Dowling et al. | |
| 2002/0066798 A1 | 6/2002 | Laudamiel-Pellet et al. | |
| 2002/0068009 A1 | 6/2002 | Laudamiel-Pellet et al. | |
| 2002/0068010 A1 | 6/2002 | Laudamiel-Pellet et al. | |
| 2002/0075677 A1 | 6/2002 | Dokupil | |
| 2002/0097978 A1 | 7/2002 | Lowry et al. | |
| 2002/0113555 A1 | 8/2002 | Lys et al. | |
| 2002/0113909 A1 | 8/2002 | Sherwood | |
| 2002/0113912 A1 | 8/2002 | Wright et al. | |
| 2002/0115905 A1 | 8/2002 | August | |
| 2002/0130146 A1 | 9/2002 | Borut et al. | |
| 2002/0136542 A1 | 9/2002 | He et al. | |
| 2002/0136886 A1 | 9/2002 | He et al. | |
| 2002/0145394 A1 | 10/2002 | Morgan et al. | |
| 2002/0159274 A1 | 10/2002 | Hubbell et al. | |
| 2002/0166871 A1 | 11/2002 | Muderlak et al. | |
| 2002/0172512 A1 | 11/2002 | Stathakis et al. | |
| 2002/0176704 A1* | 11/2002 | Roe | 392/393 |
| 2002/0179643 A1 | 12/2002 | Knight et al. | |
| 2002/0195975 A1 | 12/2002 | Schanberger et al. | |
| 2003/0012018 A1 | 1/2003 | Kluth | |
| 2003/0028260 A1 | 2/2003 | Blackwell | |
| 2003/0028888 A1 | 2/2003 | Hunter et al. | |

| | | | | | | |
|---|---|---|---|---|---|---|
| 2003/0029918 A1 | 2/2003 | Leanheart et al. | | 2005/0062440 A1 | 3/2005 | Lys et al. |
| 2003/0030808 A1 | 2/2003 | Marshall et al. | | 2005/0063194 A1 | 3/2005 | Lys et al. |
| 2003/0035917 A1 | 2/2003 | Hyman | | 2005/0068777 A1 | 3/2005 | Popovic |
| 2003/0057887 A1 | 3/2003 | Dowling et al. | | 2005/0069304 A1 | 3/2005 | He et al. |
| 2003/0063902 A1 | 4/2003 | Pedrotti et al. | | 2005/0069306 A1 | 3/2005 | He et al. |
| 2003/0076281 A1 | 4/2003 | Morgan et al. | | 2005/0069307 A1 | 3/2005 | He et al. |
| 2003/0137258 A1 | 7/2003 | Piepgras et al. | | 2005/0099824 A1 | 5/2005 | Dowling et al. |
| 2003/0138241 A1 | 7/2003 | Pedrotti et al. | | 2005/0105186 A1 | 5/2005 | Kaminsky et al. |
| 2003/0147243 A1 | 8/2003 | Alduby | | 2005/0105296 A1 | 5/2005 | French |
| 2003/0168524 A1 | 9/2003 | Hess et al. | | 2005/0105303 A1 | 5/2005 | Emde |
| 2003/0168751 A1 | 9/2003 | Bartsch et al. | | 2005/0116667 A1 | 6/2005 | Mueller et al. |
| 2003/0169400 A1 | 9/2003 | Buazza et al. | | 2005/0117365 A1 | 6/2005 | Menke |
| 2003/0169513 A1 | 9/2003 | Kaminsky et al. | | 2005/0122065 A1 | 6/2005 | Young |
| 2003/0169514 A1 | 9/2003 | Bourdelais et al. | | 2005/0122292 A1 | 6/2005 | Schmitz et al. |
| 2003/0175019 A1 | 9/2003 | Bresolin et al. | | 2005/0122721 A1 | 6/2005 | Hori |
| 2003/0175148 A1 | 9/2003 | Kvietok et al. | | 2005/0122722 A1 | 6/2005 | Menke |
| 2003/0194225 A1 | 10/2003 | Pedrotti et al. | | 2005/0128743 A1 | 6/2005 | Chuey et al. |
| 2003/0194355 A1 | 10/2003 | Pedrotti et al. | | 2005/0128751 A1 | 6/2005 | Roberge et al. |
| 2003/0205364 A1 | 11/2003 | Sauciuc et al. | | 2005/0133617 A1 | 6/2005 | Hidalgo et al. |
| 2003/0206411 A9 | 11/2003 | Dowling et al. | | 2005/0146893 A1 | 7/2005 | Ford et al. |
| 2003/0214080 A1 | 11/2003 | Maki et al. | | 2005/0147523 A1 | 7/2005 | Laudamiel-Pelleet et al. |
| 2003/0222587 A1 | 12/2003 | Dowling et al. | | 2005/0147539 A1 | 7/2005 | Laudamiel-Pellet et al. |
| 2004/0004839 A1 | 1/2004 | Souza et al. | | 2005/0151489 A1 | 7/2005 | Lys et al. |
| 2004/0007710 A1 | 1/2004 | Roy et al. | | 2005/0157499 A1 | 7/2005 | Kim |
| 2004/0007787 A1 | 1/2004 | Kvietok et al. | | 2005/0167522 A1 | 8/2005 | Wheatley et al. |
| 2004/0009103 A1 | 1/2004 | Westring | | 2005/0168986 A1 | 8/2005 | Wegner |
| 2004/0016818 A1 | 1/2004 | Murdell et al. | | 2005/0169812 A1* | 8/2005 | Helf et al. .................. 422/123 |
| 2004/0028551 A1 | 2/2004 | Kvietok et al. | | 2005/0174473 A1 | 8/2005 | Morgan et al. |
| 2004/0033067 A1 | 2/2004 | He et al. | | 2005/0174777 A1 | 8/2005 | Cooper et al. |
| 2004/0033171 A1 | 2/2004 | Kvietok et al. | | 2005/0178345 A1 | 8/2005 | Crapser |
| 2004/0035409 A1 | 2/2004 | Harwig et al. | | 2005/0180736 A1 | 8/2005 | Zobele |
| 2004/0036006 A1 | 2/2004 | Dowling | | 2005/0185392 A1 | 8/2005 | Walter et al. |
| 2004/0044106 A1 | 3/2004 | Portnoy et al. | | 2005/0185395 A1 | 8/2005 | Pinter |
| 2004/0076410 A1 | 4/2004 | Zobele et al. | | 2005/0191481 A1 | 9/2005 | He et al. |
| 2004/0090191 A1 | 5/2004 | Mueller et al. | | 2005/0194460 A1 | 9/2005 | Selander |
| 2004/0090787 A1 | 5/2004 | Dowling et al. | | 2005/0195598 A1 | 9/2005 | Dancs et al. |
| 2004/0095746 A1 | 5/2004 | Murphy | | 2005/0196159 A1 | 9/2005 | Zobele |
| 2004/0105261 A1 | 6/2004 | Ducharme | | 2005/0201107 A1 | 9/2005 | Seki |
| 2004/0105264 A1 | 6/2004 | Spero | | 2005/0201944 A1 | 9/2005 | Kvietok et al. |
| 2004/0105669 A1 | 6/2004 | He et al. | | 2005/0205916 A1 | 9/2005 | Conway et al. |
| 2004/0113568 A1 | 6/2004 | Dowling et al. | | 2005/0211790 A1 | 9/2005 | Kvietok et al. |
| 2004/0130909 A1 | 7/2004 | Mueller et al. | | 2005/0212404 A1 | 9/2005 | Chen et al. |
| 2004/0131509 A1 | 7/2004 | He et al. | | 2005/0213352 A1 | 9/2005 | Lys et al. |
| 2004/0141315 A1 | 7/2004 | Sherburne | | 2005/0213353 A1 | 9/2005 | Lys et al. |
| 2004/0141321 A1 | 7/2004 | Dowling et al. | | 2005/0214158 A1 | 9/2005 | Kvietok et al. |
| 2004/0144884 A1 | 7/2004 | He et al. | | 2005/0218243 A1 | 10/2005 | Zobele et al. |
| 2004/0145067 A1 | 7/2004 | Millan | | 2005/0218838 A1 | 10/2005 | Lys et al. |
| 2004/0150993 A1 | 8/2004 | McElhaney et al. | | 2005/0218870 A1 | 10/2005 | Lys et al. |
| 2004/0150994 A1 | 8/2004 | Kazar et al. | | 2005/0219838 A1 | 10/2005 | Belliveau |
| 2004/0155609 A1 | 8/2004 | Lys et al. | | 2005/0219872 A1 | 10/2005 | Lys et al. |
| 2004/0160199 A1 | 8/2004 | Morgan et al. | | 2005/0225856 A1 | 10/2005 | Kokuzawa et al. |
| 2004/0178751 A1 | 9/2004 | Mueller et al. | | 2005/0226788 A1 | 10/2005 | Hrybyk et al. |
| 2004/0179167 A1 | 9/2004 | Dahi et al. | | 2005/0231133 A1 | 10/2005 | Lys et al. |
| 2004/0208675 A1 | 10/2004 | Horikoshi et al. | | 2005/0232831 A1 | 10/2005 | Taylor et al. |
| 2004/0212993 A1 | 10/2004 | Morgan et al. | | 2005/0236029 A1 | 10/2005 | Dowling |
| 2004/0240890 A1 | 12/2004 | Lys et al. | | 2005/0236998 A1 | 10/2005 | Mueller et al. |
| 2004/0247300 A1 | 12/2004 | He et al. | | 2005/0248299 A1 | 11/2005 | Chemel et al. |
| 2004/0249094 A1 | 12/2004 | Demain | | 2005/0253533 A1 | 11/2005 | Lys et al. |
| 2004/0257007 A1 | 12/2004 | Lys et al. | | 2005/0275626 A1 | 12/2005 | Mueller et al. |
| 2005/0002105 A1 | 1/2005 | Nemoto et al. | | 2005/0276053 A1 | 12/2005 | Nortrup |
| 2005/0024868 A1 | 2/2005 | Nagai et al. | | 2005/0285547 A1 | 12/2005 | Piepgras |
| 2005/0029688 A1 | 2/2005 | Hagmann et al. | | 2006/0002110 A1 | 1/2006 | Dowling et al. |
| 2005/0030744 A1 | 2/2005 | Ducharme | | 2006/0012987 A9 | 1/2006 | Ducharme |
| 2005/0035728 A1 | 2/2005 | Schanberger et al. | | 2006/0016960 A1 | 1/2006 | Morgan et al. |
| 2005/0036300 A1 | 2/2005 | Dowling et al. | | 2006/0193611 A1 | 8/2006 | Ruiz Ballesteros et al. |
| 2005/0040774 A1 | 2/2005 | Mueller et al. | | 2006/0231213 A1 | 10/2006 | Matsuda et al. |
| 2005/0041161 A1 | 2/2005 | Dowling et al. | | | | |
| 2005/0041424 A1 | 2/2005 | Ducharme | | FOREIGN PATENT DOCUMENTS | | |
| 2005/0044617 A1 | 3/2005 | Mueller et al. | | | | |
| 2005/0047132 A1 | 3/2005 | Dowling et al. | | DE | 3701499 | 7/1988 |
| 2005/0047134 A1 | 3/2005 | Mueller et al. | | DE | 4131613 | 3/1993 |
| 2005/0053368 A1 | 3/2005 | Pesu et al. | | DE | 4446413 | 12/1994 |
| 2005/0053528 A1 | 3/2005 | Rymer | | EP | 0 252 642 | 1/1988 |

| | | |
|---|---|---|
| EP | 0 362 397 | 4/1990 |
| EP | 0537130 B1 | 4/1993 |
| EP | 0548274 B1 | 6/1993 |
| EP | 0617667 A1 | 10/1994 |
| EP | 0705281 A1 | 4/1996 |
| EP | 0736248 A1 | 10/1996 |
| EP | 0945062 B1 | 9/1999 |
| EP | 0956868 B1 | 11/1999 |
| EP | 1 033 139 | 9/2000 |
| EP | 1 184 083 A1 | 3/2002 |
| EP | 1 219 308 | 7/2002 |
| EP | 1332765 A1 | 8/2003 |
| EP | 1422249 A1 | 5/2004 |
| ES | 1005422 | 11/1988 |
| ES | 1015255 | 6/1991 |
| FR | 2581878 | 11/1986 |
| GB | 2181649 | 4/1987 |
| GB | 2277267 A | 10/1994 |
| GB | 2369816 A | 6/2002 |
| JP | 54-21247 | 2/1979 |
| JP | 06-36643 | 2/1985 |
| JP | 62094169 | 4/1987 |
| JP | 1295808 | 11/1989 |
| JP | 2078077 U | 6/1990 |
| JP | 2242633 | 9/1990 |
| JP | 2138577 U | 11/1990 |
| JP | 3240701 | 10/1991 |
| JP | 5003744 | 1/1993 |
| JP | 6003627 | 1/1994 |
| JP | 6155489 | 6/1994 |
| JP | 6205929 | 7/1994 |
| JP | 06-262057 | 9/1994 |
| JP | 07-009744 | 2/1995 |
| JP | 7230847 | 8/1995 |
| JP | 08-084551 | 4/1996 |
| JP | 08-241039 | 9/1996 |
| JP | 8278413 | 10/1996 |
| JP | 09-074971 | 3/1997 |
| JP | 09-075437 | 3/1997 |
| JP | 9107861 | 4/1997 |
| JP | 308422 | 12/1997 |
| JP | 10014467 | 1/1998 |
| JP | 10057464 | 3/1998 |
| JP | 2004057548 | 2/2004 |
| JP | 2004275371 | 10/2004 |
| WO | WO 91/15249 | 10/1991 |
| WO | WO 96/04021 | 2/1996 |
| WO | WO 97/13539 | 4/1997 |
| WO | WO 97/22324 | 6/1997 |
| WO | WO 98/19526 | 5/1998 |
| WO | WO 98/58692 | 12/1998 |
| WO | WO 01/43785 A1 | 6/2001 |
| WO | WO 01/79752 | 10/2001 |
| WO | WO 02/09772 | 2/2002 |
| WO | WO 03/095334 | 11/2003 |
| WO | WO 03098971 A1 | 11/2003 |
| WO | WO 2004071935 A2 | 8/2004 |
| WO | WO 2005/030276 | 4/2005 |
| WO | WO 2005/092400 | 10/2005 |

OTHER PUBLICATIONS

Office Action in U.S. Appl. No. 11/096,934 dated Jul. 30, 2007.
Office Action in U.S. Appl. No. 11/096,753 dated Oct. 2, 2006.
Office Action in U.S. Appl. No. 11/096,753 dated May 3, 2007.
Office Action in U.S. Appl. No. 11/096,753 dated Oct. 29, 2007.
Office Action in U.S. Appl. No. 11/096,753 dated Apr. 3, 2008.

* cited by examiner

COORDINATED EMISSION OF FRAGRANCE, LIGHT, AND SOUND

BACKGROUND OF THE INVENTION

1. Field of the Invention

This invention relates to the integrated presentation of ambient conditions, including various combinations of aroma, light, and sound. More particularly, this invention relates to the controlled and coordinated emission of light and fragrance into a given area such as a room or a region of a yard to create a desired atmosphere within the given area. Even more particularly, this invention relates to the combined presentation of at least two of light, sound, and aroma to produce a desired sensory effect on persons within a given area, through a network of devices for providing fragrance, light, and sound, or a single device which coordinates the emission of the same.

2. Description of the Related Art

Automatic light controllers for controlling ambient light in a room are well known. Also known are devices for controlling the temperature and/or humidity in a room and devices for controlling a fragrance to be dispensed in a room. In addition, acoustic generators for generating soothing natural sounds and/or music are also known.

Lighting devices which emit different colored light, such as from light emitting diodes (LEDs) are generally known, as demonstrated with respect to the use of multiple light emitting diodes (LED's) in a single unit, as disclosed in U.S. Pat. No. 6,149,283. Illumination arrangements which are controlled remotely are disclosed in U.S. Pat. Nos. 6,016,038; 6,150,774; 6,166,496; 6,211,626; 6,292,901; and 6,340,868.

With respect to the many devices known for dispensing fragrance, U.S. Pat. No. 5,382,410 discloses an electrostatic vapor/aerosol generator for supplying aromatic oil, deodorant, disinfectant, fumigant, fungicide, insecticide or bactericide to a room. U.S. Pat. No. 4,702,418 discloses an adjustable aerosol dispenser for supplying different amounts of a fragrance into a room according to sensed light, odor, sound, etc., within the room. U.S. Pat. No. 5,115,975 discloses a device for emitting a vaporized substance into the atmosphere according to the setting of a timer. U.S. Pat. No. 6,135,369 discloses an electrostatic sprayer which can spray insecticides, which can be controlled according to selected on times and off times, and which incorporates a sensor to sense the available power for continued operation. U.S. Pat. No. 4,689,515 discloses an ultrasonic liquid atomizer with automatic frequency control. U.S. Pat. No. 3,543,122 and Pat. No. 3,615,041 disclose aerosol dispensers having timers for controlling the operation of the dispensers according to preset times.

Acoustic generators for generating sound and/or playing sounds/music stored in a memory are known in the art. These can be found in conventional clock radios, such as described in U.S. Pat. No. 5,483,689. Other examples of acoustic generators may be found in U.S. Pat. Nos. 5,452,270 and 6,423,892.

The known multicolor lighting, sound, and atmospheric control devices, however, are independently constructed and it is difficult to control the resultant overall effect when several of these devices are used in the same room or area. In addition, the prior art has been capable of producing only limited ambient effects and, consequently, the conditions which have been produced by prior art arrangements are normally recognized as being artificial and not natural. The known devices also do not provide multiple coordinated functions, such as multicolor lighting control together with controlled emission of a fragrance to produce a light presentation with accompanying fragrance variance.

There are, however, plug-in night lights known in the art which dispense fragrance. An example of this type of device can be found in U.S. Pat. No. 6,478,440. Nevertheless, devices of this nature provide limited control of ambient conditions and do not allow for coordinated presentations of various mixtures of light, sound, and aroma.

In addition, U.S. Pat. No. 6,554,203 discusses triggering a fragrance based on a signal related to the change of a movie frame or the like. U.S. Pat. No. 5,734,590 discusses triggering an aroma based on a "utility signal." Again, however, these patents do not describe a device, or network of devices, that allows for the setting and/or programming of a fully coordinated presentation of light, sound, and aroma as detailed below.

SUMMARY OF THE INVENTION

According to one aspect, our invention provides novel methods and apparatuses for producing desired ambient conditions in a given area such as a room or a yard. These novel methods and apparatuses involve an electrically controlled light emitting device which is located to emit visible light into the given area; an electrically controlled fragrance dispenser which is also located to emit a fragrance into the given area; and a controller which is constructed and connected to control the operation of the light emitting device and the fragrance dispenser in a coordinated manner such that a desired combination of light and fragrance is emitted into the area. The controller is constructed and operated to cause the light emitting device and the fragrance dispenser to emit light and fragrance in coordination with each other over a period of time.

In a more specific aspect, our invention involves the provision of several light emitting devices and several fragrance dispensers which are connected to be controlled by a common controller to provide an overall desired ambient effect in the area.

In another specific aspect, our invention involves the use of a timer to control the coordinated operation of the light emitting devices and fragrance dispensers over a period of time according to a predetermined program.

In addition, our invention may involve a presentation which simultaneously stimulates the senses of sight, sound, and smell in an integrated manner. By stimulating a greater number of senses, the presentation is made to appear more natural and not artificial.

According to another aspect of our invention, there is provided a novel method for presenting, in an enclosed area such as a room, a combined presentation of light, sound, and aroma to produce a desired overall sensory effect on persons within the room. This novel method comprises the steps of providing in the room, a plurality of controllable lamps, controllable acoustical generators, and controllable fragrance dispensers. The operation of the lamps, acoustical generators, and fragrance dispensers are then controlled in an integrated manner according to a predetermined program so as to produce the desired sensory effect.

According to yet another aspect of our invention, there is provided a novel apparatus for presenting, in an enclosed area such as a room, a combined presentation of light, sound, and aroma to produce a desired overall sensory effect on persons within the room. The novel apparatus comprises a plurality of controllable lamps, controllable acoustical generators, and controllable fragrance dispensers, all located in the room. A programmed controller is also provided in the room. The controller is programmed and is connected to control the operation of the lamps, acoustical generators, and fragrance dispensers in an integrated manner to produce the desired sensory effect.

According to another aspect of our invention, there is provided a novel apparatus for producing a combined presentation, which comprises a fragrance dispenser and a light source. The fragrance dispenser is refillable and has a fragrance controller for adjusting the rate at which the fragrance dispenser dispenses a fragrance. The light source comprises a plurality of LEDs of at least two different colors and a light controller for controlling the operation of the plurality of LEDs. In addition, the fragrance controller and the light controller are positioned in a single housing. Preferably, the fragrance controller and the light controller communicate so as to work in synchronization with each other.

The apparatus may further include a processor for controlling the operation of the light controller and fragrance controller to control the light source and the fragrance dispenser to produce a predetermined presentation over a set period of time. The predetermined presentation may set the rate at which the fragrance dispenser dispenses fragrance over the course of the presentation, and vary at least one of the color and intensity of at least one of the plurality of LEDs over the course of the presentation.

Alternatively, or additionally, the processor may be programmable, so as to allow a user to program the operation of the fragrance controller and light controller to control both the light source and the fragrance dispenser to produce a desired presentation over a set period.

The apparatus may also include an acoustical generator for generating sounds. In addition, the apparatus may include a memory for storing audio files. The acoustical generator may be controlled in manners similar to those discussed above with respect to the fragrance dispenser and light source. Accordingly, sound may be incorporated into the predetermined or user-programmed presentations.

According to another aspect of our invention, there is provided a novel apparatus for producing the combined presentation, which comprises a fragrance dispenser, a light source, and a microprocessor. The fragrance dispenser is refillable and controllable, so as to adjust the rate at which the fragrance dispenser dispenses a fragrance. The light source includes a plurality of LEDs of at least two different colors and is controllable so as to adjust the operation of the plurality of LEDs. The microprocessor controls the rate at which the fragrance dispenser dispenses fragrance and the operation of the light source.

This embodiment may also include a memory for storing a program for causing the microprocessor to control the light source and the fragrance dispenser to produce a predetermined presentation. In addition, the microprocessor may be programmable by a user. The apparatus may also include an acoustical generator for incorporating sound into the programmed or preset presentations.

According to yet another aspect of our invention, there is provided a novel apparatus for producing the combined presentation, which comprises a plurality of fragrance dispensers, a light source, and a microprocessor. The plurality of fragrance dispenser are each refillable and separately controllable, so as to adjust the rate at which each of the fragrance dispenser dispenses fragrance. The light source comprises a plurality of LEDs of at least two different colors and is controllable so as to adjust the operation of the plurality of LEDs. The microprocessor controls the rate at which each fragrance dispenser dispenses the fragrance and the operation of the light source.

Again, this embodiment may also include a memory for storing a program for causing the microprocessor to control the light source and the fragrance dispenser to produce a predetermined presentation. In addition, the microprocessor may be programmable by a user. The apparatus may further include an acoustical generator for incorporating sound into the programmed or preset presentations. In this embodiment, however, the program can control how and when a plurality of different fragrances may be emitted during a given presentation.

The fragrance dispenser (or dispensers) used in any one of the embodiments of our invention may dispense fragrance using a piezoelectrically actuated atomization device, a heat-assisted evaporation device, a fan-assisted evaporation device, among other know fragrance dispensing devices. Also, any one of the embodiments may also include a sensor for controlling operation of the apparatus. For instances, the apparatus may include a photosensor which detects light, wherein the photosensor controls at least one of the fragrance emission, sound emission, and light emission. Alternatively, the apparatus may include a motion sensor which detects motion, a fragrance detector which detects a fragrance level, and/or a sound sensor for detecting sound. Any of the above-discussed embodiments may also include a timing mechanism for measuring time. Thus, a user may program the timing mechanism to cause the apparatus to emit light, sound, or fragrance at a set time.

Our invention is also directed to a single, compact apparatus that produces presentations comprising a combination of light, sound, and aroma, wherein the presentations can be programmed and stored by a user or chosen by a user from preset presentations. Further, our invention may comprise a user-programmable device which allows the user to set the light and fragrance levels (and, optionally, the operation of an audio system) or program a presentation varying those levels, wherein the light emission is dictated by pulse width modulated LEDs and the fragrance emission is dictated by one or more pulse width modulated atomizers. Our invention is also directed to controlling, individually and jointly, a pulse width modulated fragrance device and a pulse width modulated lighting device (and, optionally, an audio system) using programming means, wherein the operation of the fragrance device and lighting device may be (i) synchronized, (ii) varied (with respect to emission levels) in coordination with each other device, and (iii) programmed as a stored presentation.

DETAILED DESCRIPTION OF THE PREFERRED EMBODIMENTS

Our invention can be provided as a networked system in which a plurality of separate devices, including combinations of those for emitting light, fragrance, and sound, are commonly controlled to produce a coordinated ambient effect. Our invention can also be embodied in a single device which emits various combinations of light, fragrance, and sound.

Figure 1:
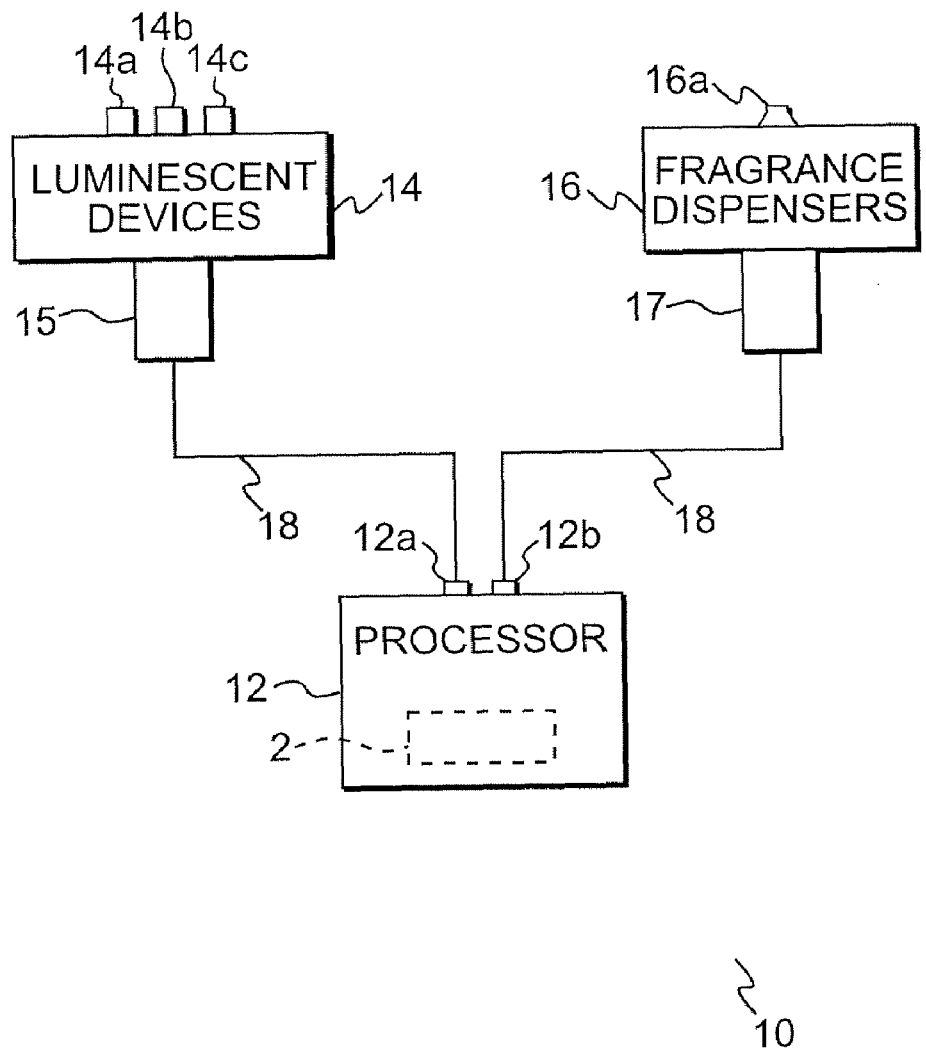
FIG. 1 is a diagrammatic plan view showing one embodiment of our invention.
Figure 2:
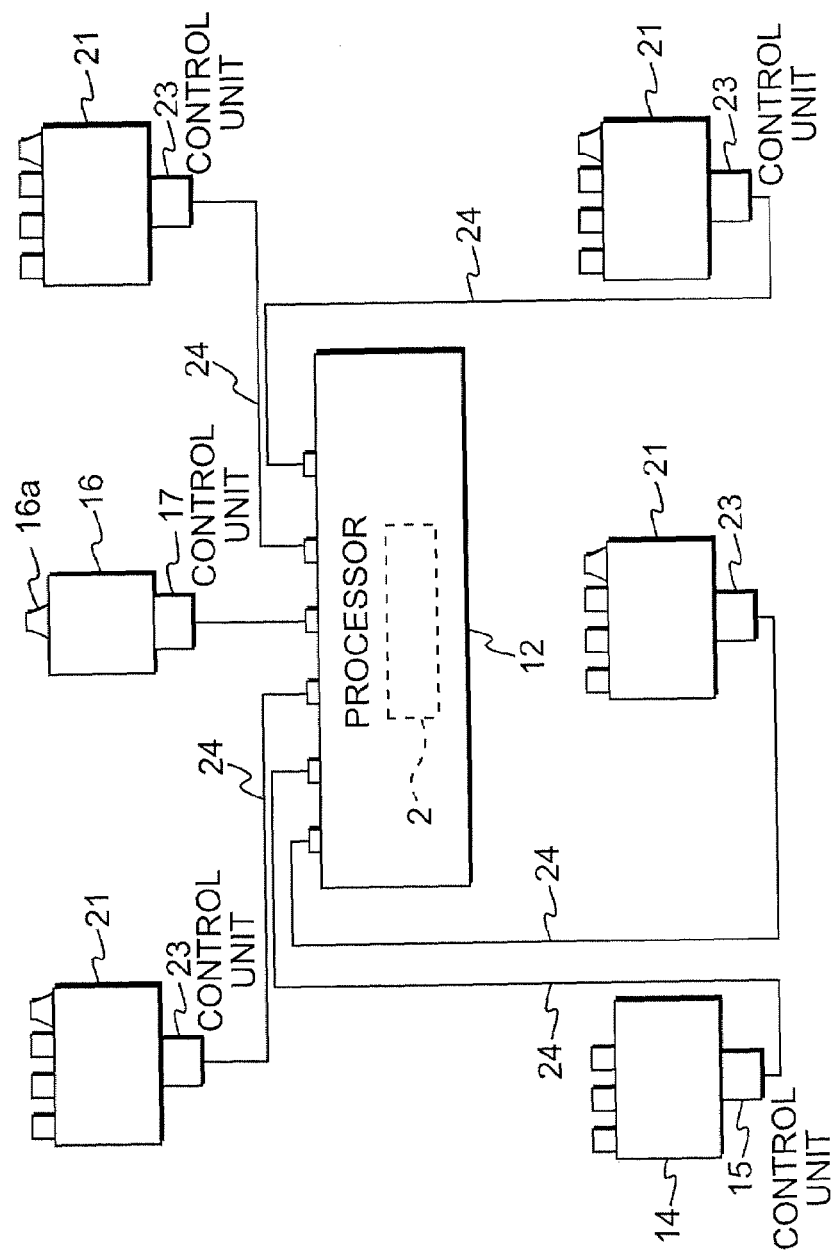
FIG. 2 is a diagrammatic plan view showing another embodiment of our invention.
Figure 3:
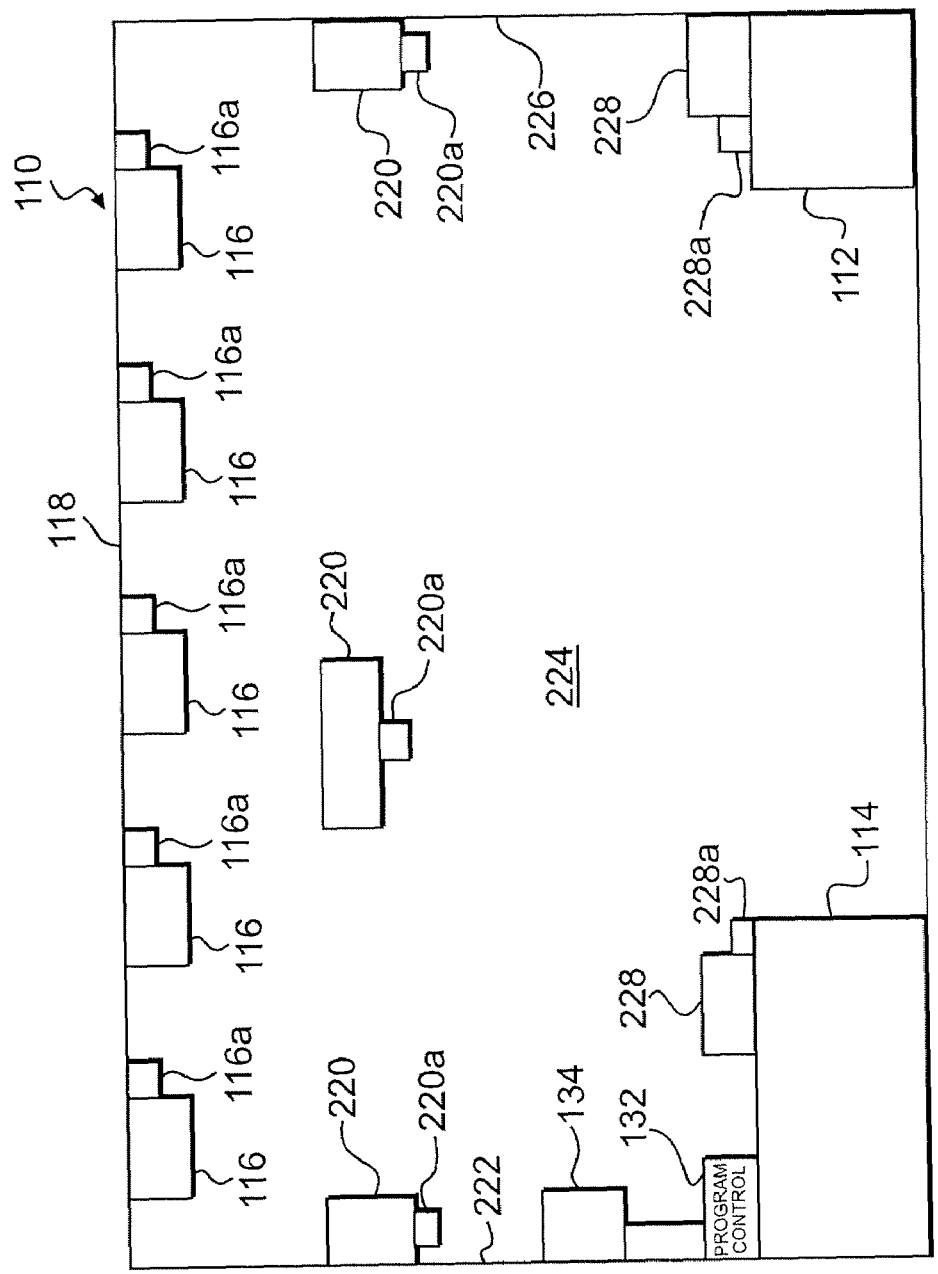
FIG. 3 is a diagrammatic representation of a room equipped with the elements of the present invention.

FIGS. 1-3 provide examples of network-type systems for producing a coordinated ambient effect. As shown in FIG. 1, there is provided in a room 10, or other area such as a yard, a processor 12, a luminescent device 14, and a fragrance dispenser 16. The luminescent device 14 is a light emitting device. In a preferred arrangement, the luminescent device 14 includes light emitting diodes (LEDs) 14a, 14b, and 14c, which emit light in different colors, respectively. However, other conventional light devices (incandescent, halogen, flourescent, etc.) may be used to provide illumination.

The fragrance dispenser 16 may hold a cartridge that contains a fragrance in any one of a number of conventional forms, including gel and liquid forms. The fragrance may be vaporized by the application of heat and ejected into the room 10 from an outlet 16a. In such a case, the dispenser 16 may have a controllable heating device to vary the rate at which vapor is driven from the fragrance or a mechanical controller for controlling the airflow around the fragrance to be vaporized (such as a shield or fan). A detailed discussion of preferred fragrance dispensers is set forth below.

The processor 12 is preferably a programmable device that produces output signals at terminals 12a and 12b according to an internal program. The output signals may be in the form of voltages or in the form of coded pulses or other coded signals which control the operation or output intensity of the luminescent device 14 and the fragrance dispenser 16. The terminals 12a and 12b may be connected by means of wires 18 to control units 15 and 17 on the luminescent device 14 and the dispenser 16. Alternatively, the processor 12 may have a single output terminal connected via a common bus to the control units 15 and 17. In such a case, the coded signals are provided with appropriate addresses to ensure that they are recognized only by the particular control unit to which they are directed. It will also be appreciated that the wires 18 and the bus could be eliminated and the coded signals with addresses from the processor 12 could be transmitted to the control units 15 and 17 by wireless means such as by infra-red light or radio signals, or be communicated over power supply lines.

The processor 12 includes an internal clock 2 to control its operation according to a controlled program. In this manner, the luminescent device 14 and the dispenser 16 are controlled to emit light and fragrances in a coordinated manner over time into the area 10 to produce a desired effect within the area.

FIG. 2 shows a second embodiment of our invention in which several luminescent devices 14 and dispensers 16 are provided and connected to be controlled in a controllable manner from a single processor 12. The embodiment of FIG. 2 may also, or alternatively, include combined luminescent devices and dispensers 21, of the type described in more detail below in connection with FIG. 4, for example. All of the devices are connected by means of wires 24 to the processor 12. Alternatively, the devices 14, 16, and 21 may communicate with the processor 12 by wireless means, such as radio, infrared or sound signals. The embodiment of FIG. 2 provides the advantage that a large area may be controlled by means of a single processor 12. Also, the processor 12 may be programmed to cause different effects to be produced in different parts of the area 10.

The devices 14, 16, and 21 may be controlled from a common bus connected to the processor 12. In such a case, the processor could be constructed to produce signals with appropriate addresses so as to control the output of desired ones of the devices 14, 16, and 21. Similarly, in the case where the signals are transmitted from the processor 12 to the devices 14, 16, and 21, such signals should be encoded with the address of the particular device to be controlled by the signals.

In another embodiment of our invention, a network-type system may further include an acoustical device for emitting sound to enhance the desired environmental effect. One example of a system combing light, aroma, and sound is shown in FIG. 3.

As shown in FIG. 3, a room 110 contains furniture 112 and 114, such as shelves or tables. Lamps 116 are shown to be mounted on the ceiling 118 of the room 110; and acoustical speakers 220 are shown to be mounted on walls 222, 224, and 226 of the room. It should be understood that the number and the placement of the lamps and speakers may be according to any arrangement which will produce a desired visual or acoustical effect. One or several fragrance dispensers 228 are provided on the furniture 112 and 114. The number of fragrance dispensers and their location should be arranged to produce a desired olfactory effect upon persons within the room 110.

The lamps 116, the acoustical speakers 220 and the fragrance dispensers 228 are each provided with associated receivers 116a, 220a, and 228a for receiving control signals which control the individual operation of each lamp, speaker, and fragrance dispenser. A program control 132 is shown on the furniture 114, although the particular location is not important. For example, the program control 132 may be mounted on one of the walls 222, 224, or 226. As can be seen, the program control 132 is connected to a transmitter 134 which is shown to be mounted on the wall 226. The transmitter is constructed to produce control signals which are received by the individual lamps 116, speakers 220, and dispensers 228. The program control operates according to a predetermined program to produce control signals which are coded to identify and to control the operation of each of the lamps 116, speakers 220, and dispensers 228. These control signals are sent from the program control 132 to the transmitter 134. The transmitter 134 in turn transmits these control signals to the appropriate lamps, speakers, and fragrance dispensers to control their operation. The signals from the transmitter to the individual lamps 116, speakers 220, and dispensers 228 may be transmitted via wires, in which case individual wires must be connected between the transmitter 134 and the receivers 116a, 220a, and 228a of the respective lamps, speakers, and dispensers. Alternatively, the signals may be transmitted in a wireless manner and may be in the form of coded infrared, optical, acoustical or radio signals.

It will be appreciated that the program can be set to operate the lamps, speakers, and fragrance dispensers in any desired manner to produce a desired overall sensory effect. In some cases, for example, the fragrance dispensers 228 may be operated only with the lamps 116 while in other cases the fragrance dispensers 228 may be operated only with the speakers 220.

The arrangement, number, and type of lamps, speakers, and fragrance dispensers to be used depends on the particular type of ambient condition to be achieved. For example, the lamps 116 may be of a type that will produce different colors or other visual effects in the room 110. Also, the speakers 220 may be connected to produce particular sounds, such as that made by wind, sea, birds, or animals. Also, the speakers 220 may be connected to produce music or other man-made sounds. The fragrance dispensers 228 may be provided with different fragrances to be emitted in particular areas of the room at different times. The output intensities of the individual lamps, speakers, and fragrance dispensing devices may also be programmed to produce variable effects; and selected ones of each may be turned off and on to change the overall ambient conditions in the room.

The control program 132 may be factory set or it may be made to be set by the user. It will be understood that the control program may be set to activate any combination of lamps, speakers and/or dispensers, according to the particular ambient condition to be produced. Further, the program control 132 may be overridden manually in the event that a preprogrammed setting is not desired. The programming may be achieved by use of well known electronic techniques and control equipment. Examples of preferred programming is discussed in more detail in subsequent sections.

Other than network-type devices, our invention can also be embodied in a single unit that may emit various combinations of light, fragrance, and sound.

Figure 4:
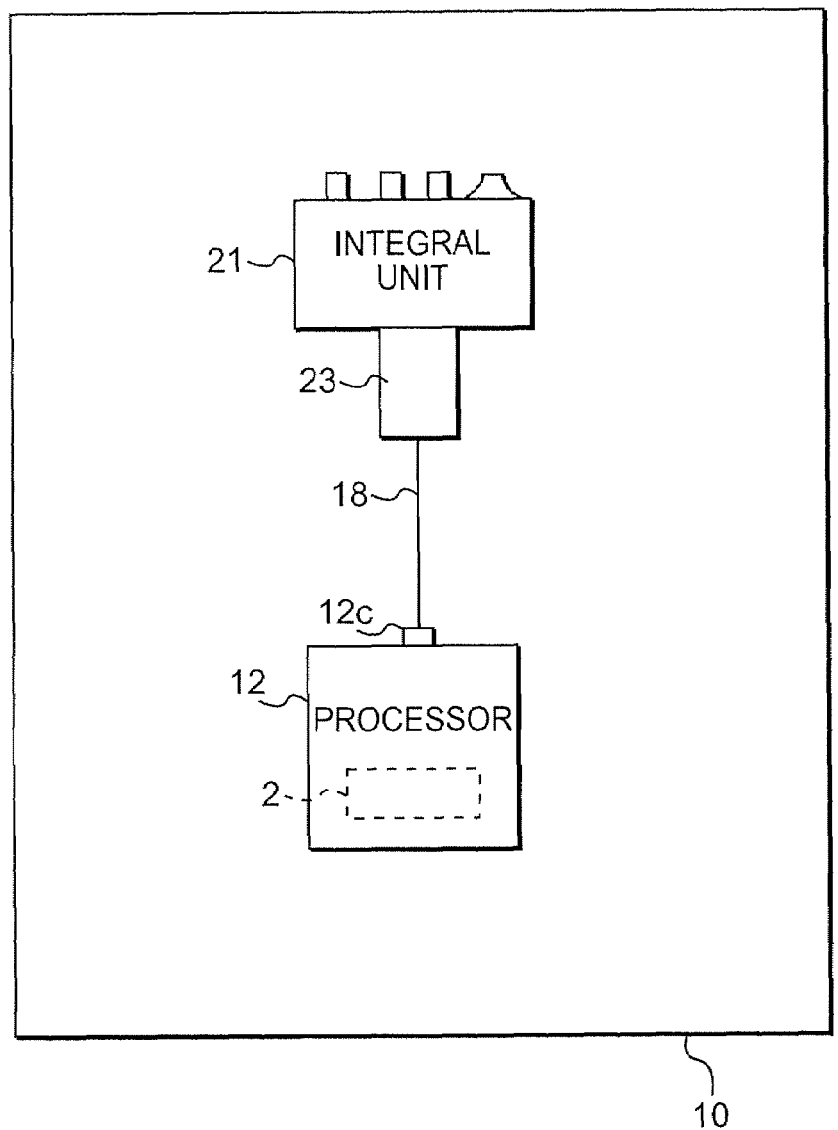
FIG. 4 is a diagrammatic plan view showing yet another embodiment of our invention.

For example, FIG. 4 shows a modification of our invention in which a luminescent device and a dispenser, as described with respect to the embodiment shown in FIG. 1, are combined into a single integral unit 21. Here, signals at a terminal 12c are transmitted via a wire 18, or in a wireless manner, to a control unit 23 on the integral unit 21. Otherwise, the system may be of the same construction as in FIG. 1. The embodiment of FIG. 4 has the advantage that fewer devices are required and their setup is simplified.

Figure 5:
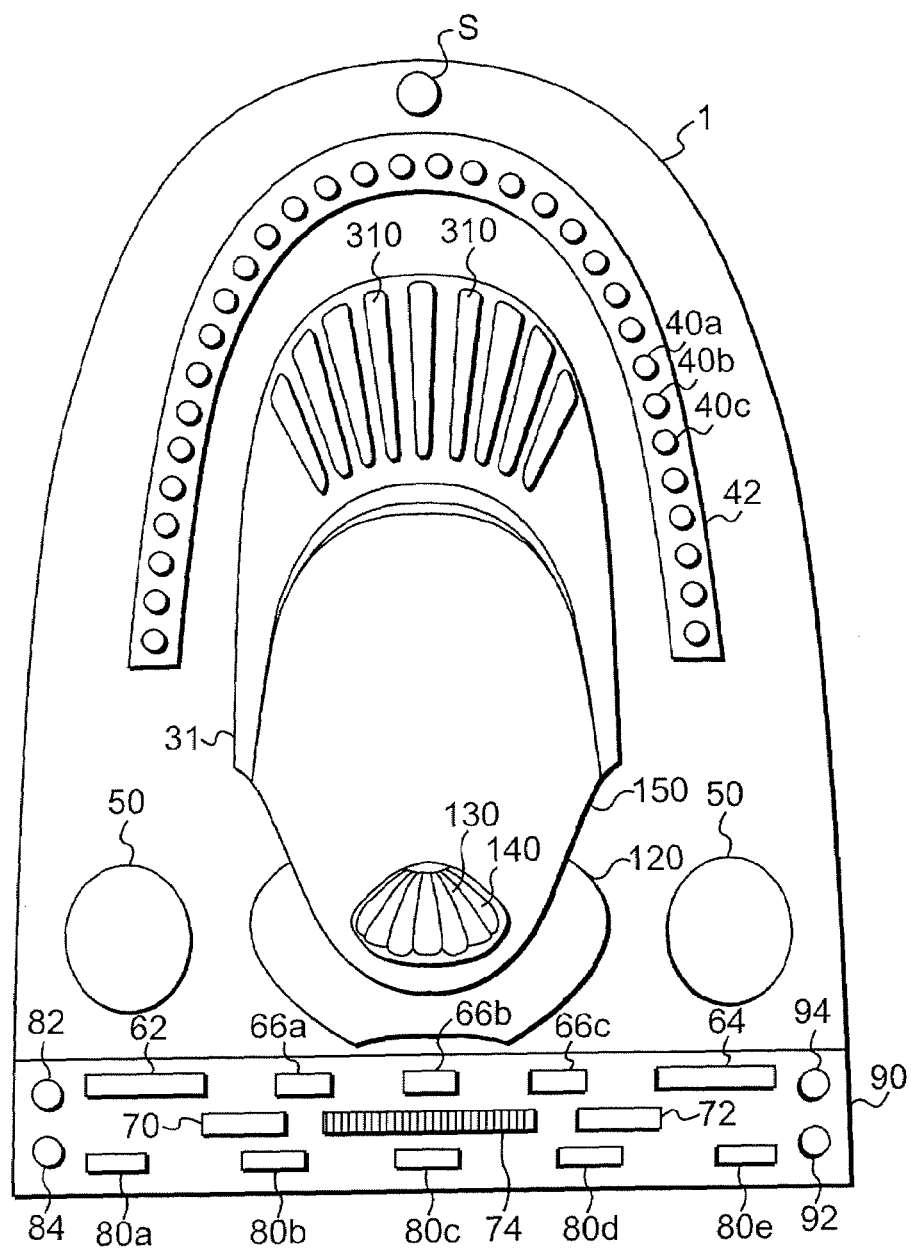
FIG. 5 is a front plan view of another embodiment of our invention.

FIG. 5 shows another embodiment of our invention in which a single presentation unit 1 emits light, fragrance, and sound. The presentation unit 1 includes a light array 42 including a plurality of different color LEDs. In particular, light array 42 includes a plurality of red LEDs 40a, blue LEDs 40b, and green LEDs 40c. The plurality of LEDs can be individually activated and controlled to adjust their respective colors and intensities. Of course, any number of different color LEDs may be provided to produce the desired light show. For simplicity sake, our invention will most often be described using a three-color arrangement. Also, other light emitting devices may be substituted, as desired.

Presentation unit 1 also includes a fragrance dispenser 31 for dispensing fragrance. The dispenser 31 includes a bottle 120, detachably retained in dispenser 31, which holds a fragrance-containing liquid. A pattern 130 on the side of the bottle 120 aligns with an opening 140 in a front shell 150 of dispenser 31. The raised pattern 130 and the opening 140 mate to cause the bottle 120 to be retained in a cavity defined by the front shell 150, so that the bottle 120 may dispense fragrance. Vents 310 may be provided to allow the passage of air across a dispensing wick (not shown) for wicking liquid from the bottle 120 to the air. The passage of air though the vents 310 may be aided by a fan, if desired. The details of the operation of fragrance dispensers such as dispenser 31 are set forth more fully below.

Presentation unit 1 also includes speakers 50 for emitting music, sounds of nature, and the like, to produce a suitable effect in connection with a light presentation by light array 42 and an aroma released from the liquid in bottle 120.

A programmable user control 90 is also provided to program the operation of light array 42, speakers 50, and fragrance dispenser 31. The user control 90 includes an on/off switch 92 which activates each of light array 42, speakers 50, and fragrance dispenser 31. Thus activated, the light array 42 sends power to the LEDs 40a-40c to produce light, speakers 50 to emit sound, and fragrance dispenser 31 to emit the fragrance from the liquid in bottle 120. The manner in which each of these systems is operated can be programmed from user control 90.

Buttons 80a-80e activate preprogrammed presentations stored in a memory to cause a processor to control each of the light array 42, speakers 50, and fragrance dispenser 31 to produce a coordinated presentation of light, sound, and aroma. Such presentations may include varying the activation, color, and intensity of LEDs 40a-40c over the course of the presentation; setting and/or varying the rate at which fragrance is dispensed from dispenser 31 over the course of the presentation; and playing a designated audio presentation through the speakers 50 over the course of the presentation.

The predetermined presentation may also be activated automatically in response to a signal from a sensor S. The sensor S may be any one of a number of sensing devices. For instance, the sensor S may be a photosensor that detects light. Accordingly, the sensor S may be set such that, when a predetermined amount of light is detected (indicating, for instance, sunset or sunrise), the sensor causes presentation unit 1 to activate one of the preprogrammed presentations stored in the memory. Other examples of suitable sensors include sensors that detect temperature, sound, movement, fragrance (i.e., a feedback loop) etc. Also, the operation and configuration of a sensing system may be made in accordance with conventional practice.

Alternatively, a user may program presentation unit 1 to produce a personalized presentation. Pressing button 62 allows a user to program the fragrance aspect of the presentation. Once button 62 has been pressed, the user can press button 82 to determine the starting rate of fragrance emission. The starting rate is set by pressing button 70 to reduce the fragrance emission rate and pressing button 72 to increase the rate. The selected rate is displayed on display 74. Once the starting rate is set, the user may press button 84 to choose an ending rate for the fragrance emission in a manner similar to that for setting the starting rate. Once set, the dispenser 31 will alter the rate of emission of fragrance over the course of the presentation from the set starting rate to the set ending rate.

By pressing buttons 66a, 66b, and 66c, a user can set the intensity of the red LEDs 40a, blue LEDs 40b, and green LEDs 40c, respectively. For instance, by pressing button 66a, the user can set the intensity of the red LEDs 40a by first pressing button 82 to set the beginning intensity and then pressing button 84 to set an ending intensity. The intensities can be adjusted during setting using buttons 70 and 72 to adjust the intensities down and up, respectively. Once set, the light array will adjust the intensities of LEDs 40a-40c over the course of the presentation.

Button 64 may be pressed to set the sound to be emitted from speakers 50. Once button 64 has been pressed, the user may press any one of buttons 80a-80e to select from different available sounds stored in a memory of presentation unit 1. The user may also set a starting volume for the chosen sound by pressing button 82 and then adjusting the volume using buttons 70 and 72 to decrease or increase, respectively, the starting volume. The ending volume may be set in a similar manner by pressing button 84 and then setting the volume again using buttons 70 and 72.

Once all of the desired settings have been programmed by the user, the user may press button 94 to begin the coordinated presentation. The duration of the presentation may be adjusted by the number of times the user presses button 94. For instance, the user may press the button once to begin a fifteen-minute presentation, but press the button twice to cause presentation unit 1 to implement the programmed presentation over a thirty-minute period.

Of course, the user may set only one of the light array 42, speakers 50, and fragrance dispenser 31, or combinations thereof to produce the desired effect. Also, FIG. 5 merely shows one potential embodiment of our invention. More complicated and involved programming systems may be provided to give the user enhanced control of the system. Also, the user may also be allowed to load personalized audio files or other formats to play specified sounds. For instance, the speakers 50 could be used to play music provided from a radio, CD player, tape cassette, MP3 player, and the like using means well known in the art.

Figure 6:
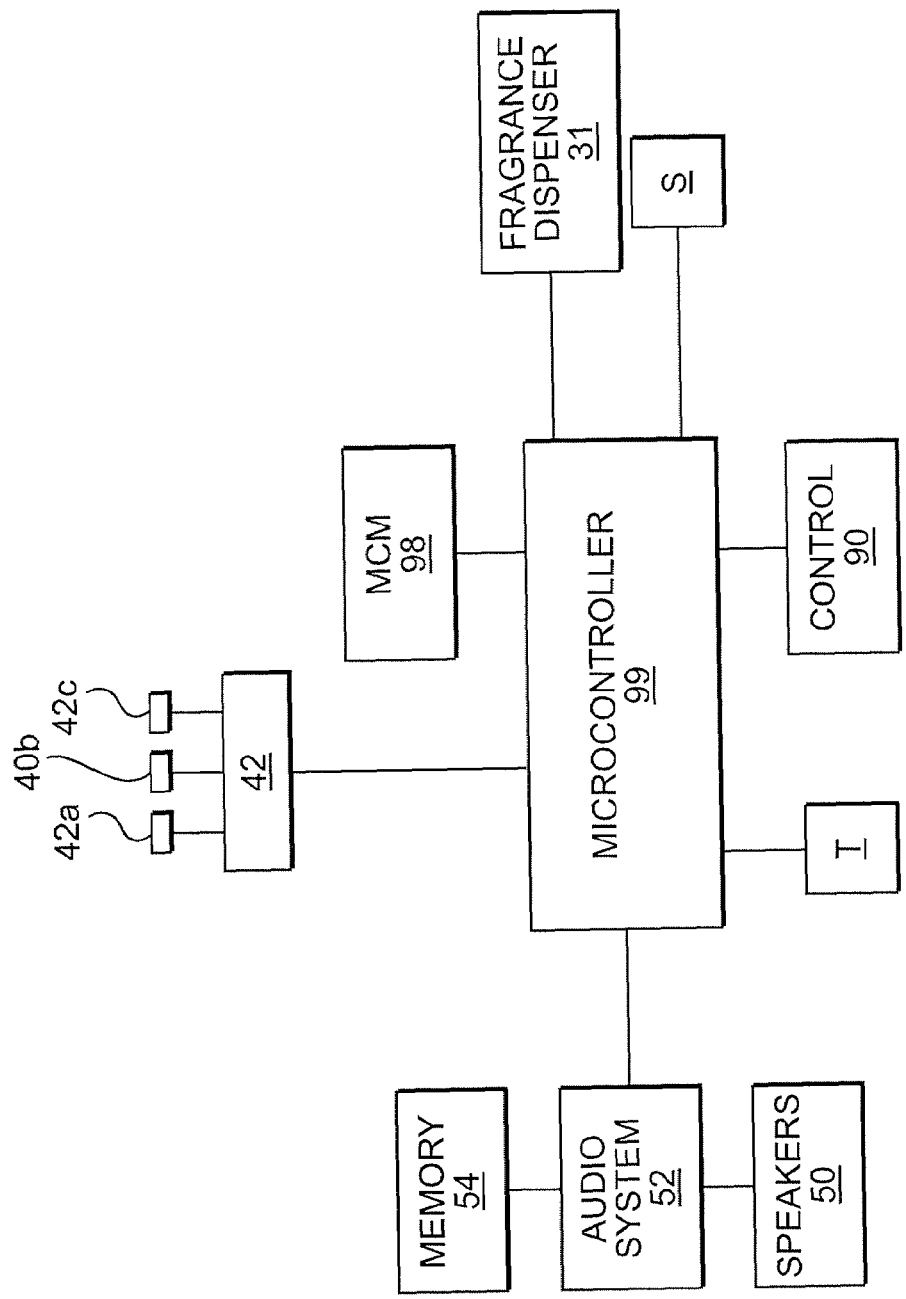
FIG. 6 is a diagrammatic plan view showing the arrangement of the components of the embodiment shown in FIG. 5.

FIG. 6 shows a diagrammatic representation of functional units of presentation unit 1. Microcontroller 99 is a programmable controller that produces output signals to control the emission of light from the LEDs of light array 42, the sounds emitted from speakers 50 of the audio system 52, and the amount of fragrance emitted from fragrance dispenser 31. Microcontroller 99 produces and outputs the signals to operate these devices according one or more programs stored in the memory 98. The signals may be in the form of voltages, coded pulses, or other coded signals which control the operation of the various components. The programs may be preset in the memory 98 and then selected and activated by a user through user control 90. Alternatively, a user may program a personalized program for controlling presentation unit 1 using user control 90 and store the program in memory 98 such that microcontroller 99 produces the same over the course of the user programmed presentation.

In running a set program stored in the memory 98, the microcontroller 99 may cause audio system 52 to play audio files stored in memory 54 through speakers 50. Also, memory 54 may be removed, in which case, memory 98 can serve the same functions of memory 54, depending on preferred design considerations.

Operation of microcontroller 99 can also be activated to produce a presentation according to a program stored in memory 98 by a signal from sensor S, as discussed above.

In addition, presentation unit 1 may include a timing mechanism T. The timing mechanism T may be an oscillator, crystal, conventional clock, etc. The timing mechanism T controls the operation of microcontroller 99 in accordance with the program from the memory 99. In addition, the timing mechanism T may be used to control the length of a presentation of light, sound, and aroma set by a program in memory 98, as programmed through user control 90. In addition, in alternative embodiments, a user may use the user control 90 to set the time at which a particular presentation stored in the memory 98 will begin.

The general design of the presentation unit 1 or network-type systems shown in FIGS. 1-3 may be varied as necessary while still keeping within the scope of our invention. Similarly, the individual components used to construct devices according to our invention may be chosen or designed in conformance with known standards by one of ordinary of skill in the art. Nevertheless, provided below is a detailed description of preferred components/configurations of our invention.

Fragrance Dispensers

Fragrance dispensers are known in the art. A variety of different types of dispensers may be used to construct our invention, including piezoelectrically actuated atomization devices, evaporation devices, heat-assisted evaporation devices, and fan-assisted evaporation devices, among others. Even within each type of dispenser, variations are possible, as would be appreciated by one of ordinary skill in the art.

Figure 7:
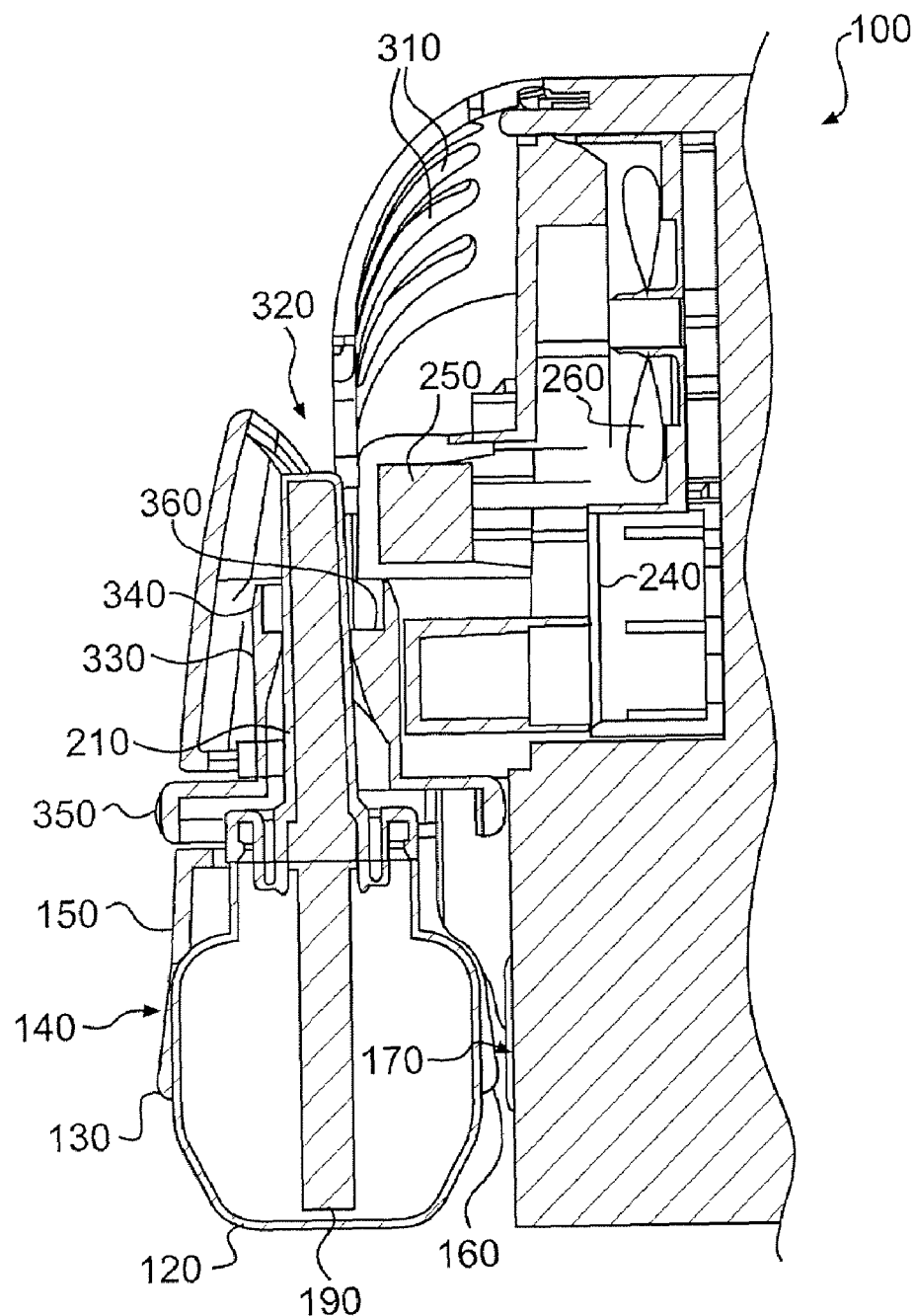
FIG. 7 is a cross section of an evaporator for use in one embodiment of our invention.

FIG. 7 shows one preferred system for dispensing fragrance that combines heat and fan-assisted evaporation. As shown in FIG. 7, an evaporator 100 comprises a bottle 120 detachably retained therein. The bottle 120 contains an evaporable substance (not shown), such as, for example, a liquid formulation including a fragrance. The term "bottle" is used herein in its broadest possible sense, including any receptacle, container, pouch, etc., capable of holding a fragrance formulation. A raised pattern 130 on one side of the bottle is engaged by an opening 140 in a front shell 150 of the evaporator 100, while a similar raised pattern 160 on an opposite side of the bottle 120 is engaged by a recess 170, in order to secure the bottle 120 within the evaporator 100. The front shell 150 is sufficiently pliant so that pulling the bottle 120 in a downward direction causes the raised patterns 130, 160 to release from the opening 140 and the recess 170, thereby enabling removal of the bottle 120 from the evaporator 100. Suitable refill bottles are available in a wide variety of liquid formulations from S.C. Johnson & Son, Inc., of Racine, Wis., under the GLADE® PLUGINS® brand name.

The bottle 120 includes a wick 190 for drawing the liquid formulation out of the bottle 120 and toward an upper portion of the wick 190. A lower portion of the wick 190 is immersed in the liquid formulation, and the upper portion of the wick 190 protrudes above the neck of the bottle 120. Preferably, the wick 190 is positioned within the bottle 120 by a cap having a sheath 210 that encases the upper portion of the wick 190, except for an open area near the tip of the wick 190. Alternatively, a cap without a sheath can be utilized. Preferably, the wick is about 7 mm in diameter and is constructed of ultra high molecular weight high density polyethylene.

A circuit board 240, connected to a power source (not shown), is electrically connected to a heating device 250 and, preferably, also to a fan unit 260. The heating device 250 is disposed adjacent the tip of the wick 190 when the bottle 120 is inserted in the evaporator 100. Heating the wick 190 enhances the rate at which the liquid formulation evaporates into the surrounding environment. Preferably, the heating device 250 is a 1.9 kΩ, 7 W metal oxide resistor potted in a ceramic block. The resistor preferably has PTC (positive temperature coefficient) characteristics, meaning that its resistance value increases slightly as the resistor heats up. Alternatively, the heating device 250 can comprise one or more other types of resistor heaters, a wire-wound heater, a PTC heater, or the like.

The fan unit 260 is disposed within an upper portion of the evaporator 100. The fan unit 260 creates an airstream that entrains the evaporated liquid formulation and assists in the dispersion of the chemical active into the surrounding environment. A suitable fan unit 260 is a 12 V, DC, brushless fan, such as available from Power Logic Tech. Inc., of Taipei-Hsien, Taiwan. Alternatively, other DC or AC fans could be utilized, with appropriate adjustments to the circuit board 240.

The front shell 150 includes a plurality of vents 310 through which the airstream exits the evaporator 100. As the airstream exits the evaporator 100 through the vents 310, it entrains the evaporated liquid formulation, which rises from the wick 190 through an opening 320 in the front shell 150 below the vents 310.

Optionally, the evaporator 100 also includes an adjustment mechanism 330 that positions the upper portion of the wick 190 with respect to the heating device 250. Preferably, the adjustment mechanism 330 includes a hollow cylindrical portion 340 that surrounds and engages part of the upper portion of the wick 190, preferably at a location where the wick 190 is encased by the sheath 210. The adjustment mechanism 330 also includes a dial portion 350, accessible from outside the evaporator housing 110, for rotating the cylindrical portion 340 about an axis of rotation. The dial portion 350 preferably is formed integrally with the cylindrical portion 340, although it need not be.

Preferably, a plurality of tapered lugs 360 are provided on the inner surface of the cylindrical portion 340. The lugs 360 are widest at their uppermost point, where they come in contact with the wick 190, and narrowest near the bottom of the cylindrical portion 340. At their uppermost point, the lugs 360 define a circular opening that is just large enough for the wick 190 to fit through. The center of this opening is offset relative to the axis of rotation of the cylindrical portion 340.

Rotating the dial portion 350 of the adjustment mechanism 330 causes the wick 190 to move toward or away from the heating device 250 in a lateral direction, i.e., in a direction substantially perpendicular to the longitudinal axis of the wick 190.

One of ordinary skill in the art will appreciate that the specific features of the evaporative-type device may be varied, while still providing acceptable fragrance dispensing action. In addition, a more detailed description of this type of fragrance dispenser may be found in U.S. patent application Ser. No. 10/267,417, filed Oct. 9, 2002.

Alternatively, and more preferably, the fragrance may be dispensed using an atomizer that releases droplets of fragrance into the air. In such a case, a fragrance is supplied in liquid form to the dispenser and is atomized in the dispenser by any of various controllable means, for example by an orifice plate that is vibrated by a piezoelectric actuator. Examples of mechanical atomization devices are shown and described in U.S. Pat. Nos. 6,292,196 and 6,341,732.

Figure 8:
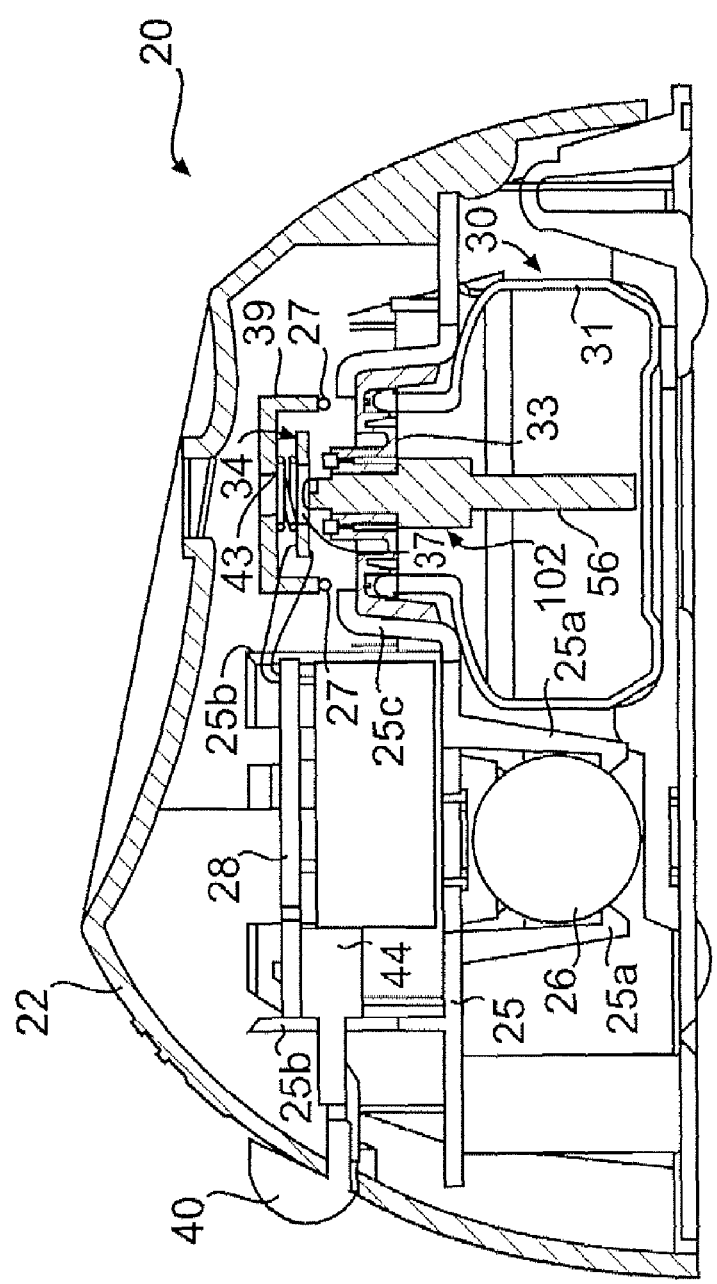
FIG. 8 is an elevational cross section of an atomizer for use in one embodiment of our invention.

In addition, FIG. 8 shows a preferred atomizer for use in our invention. As shown in FIG. 8, a piezoelectrically actuated atomization device 20 generally comprises an atomizer assembly 34, which includes an orifice plate 37, and a replaceable reservoir assembly 30. The reservoir assembly 30 includes a reservoir 31 containing fluid and a wick 56. When one reservoir assembly 30 is removed by a user and replaced with another reservoir assembly, the wick 56 instantaneously delivers fluid to the orifice plate 37.

The atomization device 20 comprises a housing 22 formed as a hollow plastic shell. A horizontal platform 25 extends across the interior of the housing 22. A battery 26 is supported by means of support prongs 25a which extend down from the underside of the platform 25 inside the housing 22. In addition, a printed circuit board 28 is supported on support elements 25b which extend upwardly from the platform 25. A liquid reservoir assembly 30 is replaceably mounted to the underside of a dome-like formation 25c on the platform 25. The liquid reservoir assembly 30 comprises a liquid container 31 for holding a liquid to be atomized, a plug 33, which closes the top of the container, and the wick 56, which extends from within the liquid container 31 through the plug 33, to a location above the liquid container 31. The plug 33 is constructed to allow removal and replacement of the complete liquid reservoir assembly 30 from the underside of the dome-like formation 25c on the platform 25. Preferably, the plug 33 and the platform 25 are formed with a bayonet attachment (not shown) for this purpose. When the replaceable liquid reservoir assembly 30 is mounted on the platform 25, the wick 56 extends up through a center opening in the dome-like formation 25c. The wick 56, operates by capillary action to deliver liquid from within the liquid container 31 to a location just above the dome-like formation 25c on the platform 25.

An atomizer assembly 34 is supported on the platform 25 in cantilever fashion by means of a resilient, elongated wire-like support 27. As is described more fully in copending U.S. patent application Ser. No. 10/304,215, filed Nov. 26, 2002, assigned to the assignee of this invention, in the preferred embodiment, the wire-like support 27 is attached at its ends to posts, which protrude upward from the platform 25. The support 27 is shaped such that it resiliently supports the lower surface of the orifice plate 37 and a spring housing 39, while a spring 43 resiliently presses on the upper surface of the orifice plate 37. (Rather than press on the orifice plate 37 itself, the spring 43 may alternatively or additionally press on a member, such as an actuator element 35, which is connected to the orifice plate 37.) Together, the support 27 and the spring 43 hold the orifice plate 37 in place in a manner that allows the orifice plate 37 to move up and down against the resilient bias of the wire-like support 27.

The atomizer assembly 34 comprises an annularly shaped piezoelectric actuator element 35 and the circular orifice plate 37, which extends across and is soldered or otherwise affixed to the actuator element 35. A construction of a vibrator-type atomizer assembly is per se well known and is described, for example, in U.S. Pat. No. 6,296,196. Accordingly, the atomizer assembly 34 will not be described in detail except to say that when alternating voltages are applied to the opposite upper and lower sides of the actuator element 35, these voltages produce electrical fields across the actuator element and cause it to expand and contract in radial directions. This expansion and contraction is communicated to the orifice plate 37 causing it to flex so that a center region thereof vibrates up and down. The center region of the orifice plate 37 is domed slightly upward to provide stiffness and to enhance atomization. The center region is also formed with a plurality of minute orifices which extend through the orifice plate 37 from the lower or under surface of the orifice plate 37 to its upper surface. A flange is provided around the center region of the dome.

In operation, the battery 26 supplies electrical power to circuits on the printed circuit board 28 and these circuits convert this power to high frequency alternating voltages. (Of course, in other embodiments, power may be provided by a power cord plugged into an electrical outlet, or by other conventional means.) A suitable circuit for producing these voltages is shown and described in U.S. Pat. No. 6,296,196, noted above. As described in that patent, the device may be operated during successive on and off times. The relative durations of these on and off times can be adjusted by an external switch actuator 40 on the outside of the housing 22 and coupled to a switch element 44 on the printed circuit board 28. In other embodiments, the on and off times may be controlled by a preset program, or controlled by a user interface working through a processor, such as user control 90 in FIG. 5.

Figure 9:
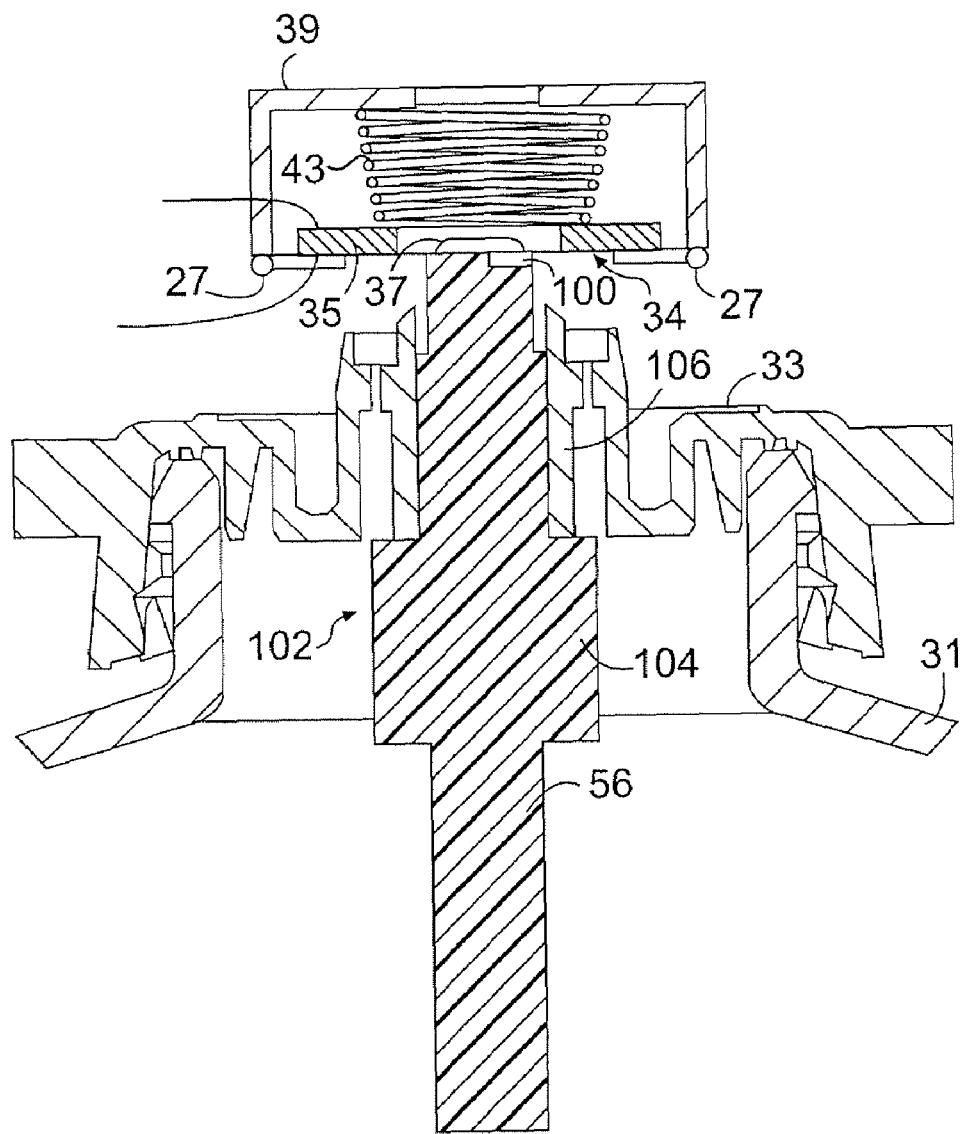
FIG. 9 is an enlarged fragmentary cross section, taken in elevation, of the upper portion of a replacement reservoir together with a vibratory-orifice-plate atomizing arrangement used in the atomizing device of FIG. 8.

When the atomizer assembly 34 is supported by the support member 27, the flange of the orifice plate 37 is positioned in contact with the upper end of the wick 56. The atomizer assembly 34 is thereby supported above the liquid reservoir assembly 30 such that the upper end of the wick 56 touches the underside of the orifice plate 37, as shown in FIG. 9. Thus, the wick 56 delivers liquid from within the liquid reservoir 31 by capillary action to the underside of the orifice plate 37, which upon vibration, causes the liquid to pass through its orifices and be ejected from its opposite side (i.e., the upper surface) in the form of very small droplets.

It will be appreciated from the foregoing that the horizontal platform 25 serves as a common structural support for both the liquid reservoir assembly 30 and the atomizer assembly 34. Thus, the horizontal platform maintains the liquid reservoir assembly 30, and particularly, the upper end of the wick 56, in alignment with the orifice plate 37 of the atomizer assembly 34. Moreover, because the atomizer assembly 34 and the orifice plate 37 are resiliently mounted, the upper end of the wick 56 will always press against the under surface of the orifice plate 37 and/or the actuator element 35 irrespective of dimensional variations which may occur due to manufacturing tolerances when one liquid reservoir is replaced by another. This is because if wick 56 of the replacement liquid reservoir assembly 30 is higher or lower than the wick 56 of the original liquid reservoir assembly 30, the action of the spring 43 will allow the orifice plate 37 to move up and down according to the location of the wick 56 in the replacement reservoir assembly 30, so that the wick 56 will always press against the underside of the orifice plate 37 and/or the actuator element 35. It will be appreciated that the wick 56 should be of a solid, dimensionally stable material so that it will not become deformed when pressed against the underside of the resiliently supported orifice plate 37.

As can be seen in FIG. 9, the wick 56 extends from inside the liquid reservoir 31 up through the plug 33 in the top of the reservoir 31 to contact the orifice plate 37 and/or the actuator element 35 from near the bottom of the liquid reservoir 31. The wick 56 has longitudinally extending capillary passages which draw liquid up from within the container 31 to the upper end of the wick 56.

The wick 56 preferably includes an integrally formed attachment assembly for securing the wick 56 to the plug 33. Of course, the attachment assembly may be a separate piece affixed to the wick 56. The attachment assembly includes a collar 102 having a lower segment 104 of a relatively large diameter and an upper segment 106 of a relatively small diameter. The top of the lower segment 104 contacts the plug 33 to prevent the wick 56 from moving out of the container 31. The upper segment 106 frictionally fits into the aperture in the plug 33.

As can be seen in FIG. 9, the upper end of the wick 56 enters into an opening in the bottom of the spring housing 39 to supply liquid to a location just below or on the bottom surface of the orifice plate 37. The wick 56 is substantially in contact with a flange portion on the periphery of the domed portion of the orifice plate 37. The wick 56 may also be in contact with the actuator element 35. However, the wick 56 includes a top surface having different levels so that a portion of the wick 56 is not in contact with the orifice plate 37 or the actuator element 35. This portion provides unobstructed passage to the atmosphere.

Again, other atomization devices may be substituted as desired in consideration of design choices, manufacturing costs, etc. Also, a more detailed explanation of the atomization device 20 may be found in copending U.S. application Ser. No. 10/412,911, filed Apr. 14, 2003.

Control Mechanisms

As discussed above, the various components for emitting light, sound, and fragrance may be configured to work in coordination with each other in any one of a number of ways, as would be appreciated by one of ordinary skill in the art. The same is true for implementing the control and programming of the various components. Nevertheless, provided below are preferred embodiments for configuring and controlling our invention.

Figure 10:
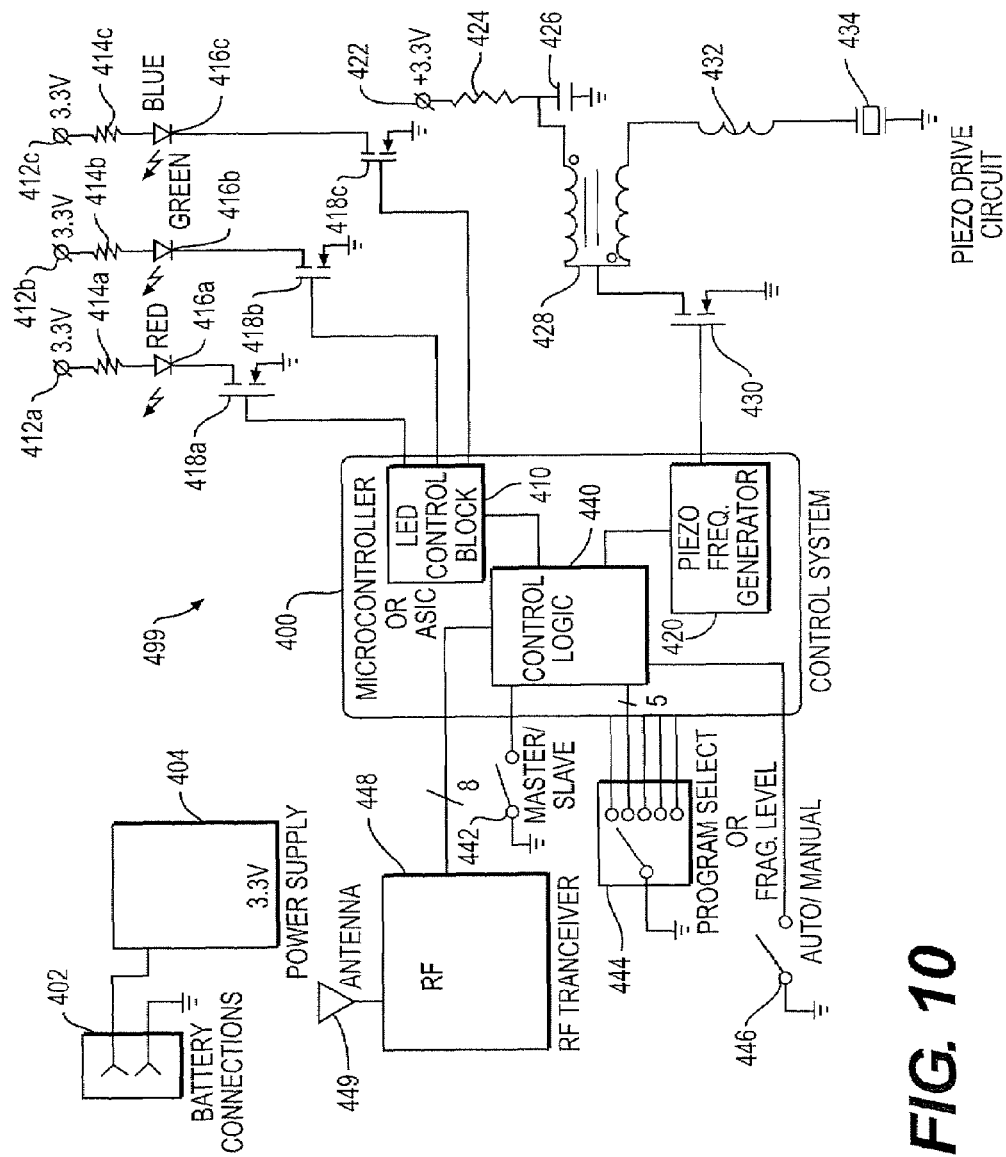
FIG. 10 is diagram of a circuit used for controlling the operation of one embodiment of our invention.

FIG. 10 shows a circuit diagram for one control arrangement for operating a presentation device 499 that produces a coordinated/combined presentation of light and fragrance. The presentation device is powered by a battery 402; however, other sources of power, such as an AC current source may be also used. A power supply 404 draws power from the battery 402 and then supplies 3.3 volts to the presentation device. In other embodiments, the current level (or voltage level) used may be altered, as desired or as necessary for the components to be powered.

A microcontroller (or ASIC) 400 controls the operation of the presentation device 499, and is powered by power supply 404. Microcontroller 400 includes a control logic 440 that provides the operational instructions to the various elements of the presentation device 499 in accordance with input signals or internal programs. The control logic 440 converts received signals or runs internal software routines to set the operation of the various elements, including an array of LEDs and a fragrance dispenser.

The control logic 440 sends a signal for controlling the operation of the array of LEDs to LED control block 410. When using pulse width modulation to drive and control the LED array, the LED control block 410 sets the duty cycles for the LEDs based on the instruction from the control logic 440.

Supply lines 412a-412c supply 3.3 volts across resistors 414a-414c, from power supply 404. Resistors 414a-414c in turn power a red LED 416a, a green LED 416b, and a blue LED 416c, respectively. Field effect transistors (FETs) 418a-418c are turned on and off in accordance with the respective duty cycles generated by the LED control block 410. Operation of the FETs 418a-418c control the LEDs 416a-416c to be activated for the portions of the duty cycle set by the LED control block 410. Thus, the intensity and color of the LEDs 416a-416c can be varied to produce the desired effects. Typically, pulse width modulation is used to control a constant current to be applied to a given diode for a set period of one duty cycle, thus controlling the total current applied to the LED over the full duty cycle. Thus, the diode flickers on for the set portion of each duty cycle, and off for the remainder of the duty cycle. Of course, this on and off operation is so fast (a typical duty cycle is in the range of a few milliseconds) that the color and intensity of the diode appears constant to an observer (with no discernable flicker), until the set period of activation over the duty cycle is changed.

While three LEDs are shown with respect to this embodiment, any number of LEDs may be used. In addition, the choice of which color LEDs to provide may be dictated by design preferences. The intensity and exact color of the LEDs may be varied by changing the current applied to each diode.

When three colors of LEDs are used, typically mixtures of red, green, and blue LEDs are preferred. Generally, one of each color LED will be provided in close proximity to one of each other color. With such an arrangement, the exact color of each diode of the set of three different colors can be adjusted to create a blended color, for example, amber or purple. This blending can be achieved by providing the three diodes in such close proximity that the observer only sees the blend of colored lights, rather than each individual diode. Alternatively, or in addition, a diffuser may be provided to diffuse the light of the three diodes to produce the combined color. In other embodiments, the lights may be projected off of a surface to be combined before being viewed by an observer.

LEDs of a wide array of colors are readily available from lighting manufactures. Also, the arrangement and operation of LEDs to achieve a desired presentation would be apparent to one of ordinary skill. Accordingly, a detailed description of specific LEDs and configurations which can be used with our invention is unnecessary.

A piezo frequency generator 420 controls the operation of a fragrance dispenser, which, in this case, is a piezoelectrically actuated atomization device. The atomization device typically operates to atomize fragrance for an approximately eleven-msec burst at set intervals. The piezo frequency generator 420 controls the frequency of the eleven-msec bursts to adjust the rate at which the fragrance is dispensed (thus, controlling the potency of the aroma). Again, typically, the piezo frequency generator 420 will operate using pulse width modulation.

A supply line 422 provides power from power supply 404 across resistor 424. The power is supplied across resistor 424 to a capacitor 426, causing the voltage stored in the capacitor 426 to rise to 3.3 volts, at which point the power flow to the capacitor 426 stops and the capacitor 426 supplies current through transformer 428 to ground, charging the transformer 428. A pulse from the piezo frequency generator 420, set in accordance with the instructions from the control logic 440, controls the FET 430 to open and close. When FET 430 is closed, the current from transformer 428 is pushed through inductor 432, which smooths the current from a square wave to a sine-like wave. The current then passes to a piezo 434, causing the device to vibrate and to release a puff of fragrance, as discussed above.

The control logic 440 may be programmed/controlled in any number of ways. The control logic 440 may first be controlled via a master/slave switch 442. When switch 442 is set in the slave position, control logic 440 is provided with external signals for setting operation of the presentation devices 499. For instance, when a plurality of individual presentation device 499 are being used, one can be designated a master, and the rest slaves. The slave devices receive signals from the master dictating the operation of each slave. The signals may be provided from the master to the slaves through any one of a number of systems, including infrared signals, hard-wired connections, radio signals, and the like. In the control embodiment shown in FIG. 10, an RF transceiver 448 is provided to send and to receive radio signals.

Alternatively, the master device may be a remote control, rather than another presentation device 499.

When switch 442 is in the slave position, the RF transceiver 448 receives an external signal, through an antenna 449, from a remote control, a master-designated presentation device 499, or the like. That signal is transmitted from the RF transceiver 448 to control logic 440 to set the presentation of light and sound through the LED control block 410 and the piezo frequency generator 420. When switch 442 is in the master position, the operation of the control logic is set by an internal program at this presentation device 499, such that microcontroller 400 acts as the master. In this case, the operational program from control logic 440 is sent to the RF transceiver 448 and broadcast to slave devices via the antenna 449.

Alternatively, an auto/manual switch 446 may be operated to override a slave designation by switch 442 or a set internal program to allow a user to manually set the fragrance output and light show. In this case, a program select switch 444 may be operated by a user to set a light show program for the LEDs 416a-416c, a fragrance level to be dispensed by the operation of the piezo 434, or a combination thereof.

Figure 11:
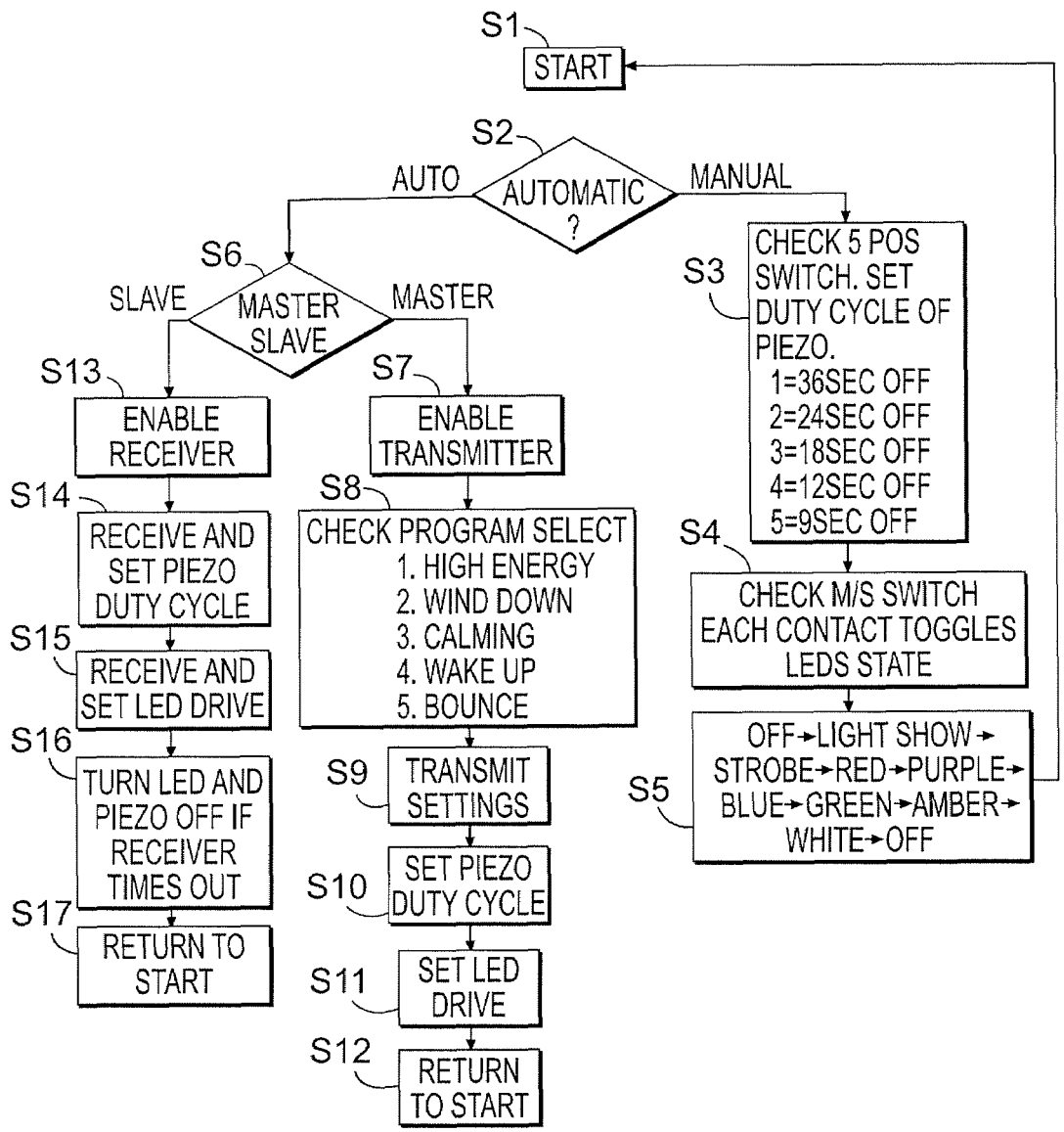
FIG. 11 is a flow chart showing the operation of a program for controlling the circuit shown in FIG. 10.

FIG. 11 shows one potential program for operating the control system shown in FIG. 10. Again, however, this is only one way of implementing control of an embodiment of our invention. One of ordinary skill in the art will appreciate that a wide variety of programs may be implemented to produce the desired control over the presentation of coordinated light and aroma.

The program starts operation of the device at step S1. At step S2, it is determined whether operation of the microcontroller 400 is to be set manually by a user or automatically with a set program. If manual operation is selected, the program proceeds to step S3. In step S3, the setting of the five-position switch 444 is checked to set the duty cycle for operating the piezo 434. For instance, in a first switch setting, the piezo 434 is activated to release fragrance every thirty-six seconds; in a second switch setting, the piezo 434 is activated to release fragrance every twenty-four seconds; in a third switch setting, the piezo 434 is activated to release fragrance every eighteen seconds; in a fourth switch setting, the piezo 434 is activated to release fragrance every twelve seconds; and in a fifth switch setting, the piezo 434 is activated to release fragrance every nine seconds. In step S4, the operation of the master/slave switch 442 is checked. The system is set such that different preprogrammed light shows are selected depending on how many times a user toggles the switch 442. Step S5 sets the light show from among an off setting, a variant light show, a strobe setting, emission of red light, emission of purple light, emission of blue light, emission of amber light, and emission of white light, depending on the toggling of switch 442.

If the automatic mode is set in step S2, the program proceeds to step S6, in which it is determined whether the microcontroller 400 is set as a master or a slave. If it is set as a master, the program proceeds to step S7 to enable the RF transceiver to transmit the program to slave devices. In step S8, a program selection is checked from among five different programs to be selected. The five programs may be selected by setting switch 444. The different programs include a "high energy" program in which the piezo 434 is set to emit fragrance every nine seconds and the LEDs perform a programmed light show. A "wind down" program sets the fragrance device to decrease from a high setting to a low setting over a two hour period, and sets the LEDs to change from emission of white light of a high intensity to emission of blue light of a low intensity, also over a two hour period. A "calming" program begins with a low fragrance emission rate and a blue light, and varies the intensity of both over the course of a thirty-minute cycle. A "wake-up" program changes from a low fragrance intensity to a high fragrance intensity, and from a low intensity blue light to a high intensity white light, over a forty-five-minute period. Also, in the "wake-up" program, the intensities (fragrance and light) and colors of a master and slave device proceed in inverse relation to each other over the course of the presentation. So, as the color emitted from the LEDs of the master changes from white to blue, the color in the slave changes from blue to white. A "bounce" program causes a master device to emit purple light and a medium level of fragrance for fifteen minutes while the slave devices are shut down. After the fifteen minutes, the master shuts down and a slave device emits the purple light and medium level of fragrance. The "bounce" program continues by causing a different device in the master-slave system to activate every fifteen minutes, with the other devices lying dormant.

Of course, a user can adjust the operation of the program by setting switch 442 in the master position, setting switch 446 in the manual position, and setting a desired fragrance level and a desired lighting scheme with switch 444.

In step S9, the set program is transmitted to RF transceiver 448 to be sent to the slave devices, and LED control block 410 and piezo frequency generator 420, to set the presentation. In step S10, the piezo duty cycle is set in piezo frequency generator 420. In step S11, the LED duty cycles are set in LED control block 410, based on the set presentation. In step S12, if the presentation has timed out, the program returns to the start at S1.

If the slave setting is set at step S6, the program proceeds to step S13, in which RF transceiver 448 is enabled to receive a signal from a master device. In step S14, the piezo frequency generator 420 sets a duty cycle in accordance with a signal received from the master device. In step S15, the LED control block 410 sets duty cycles for the LEDs based on the received signal from the master device. In step S16, the piezo frequency generator 420 and LED control block 410 turn off if the RF transceiver 448 times out. In step S17, the program returns to the start.

Figure 12:
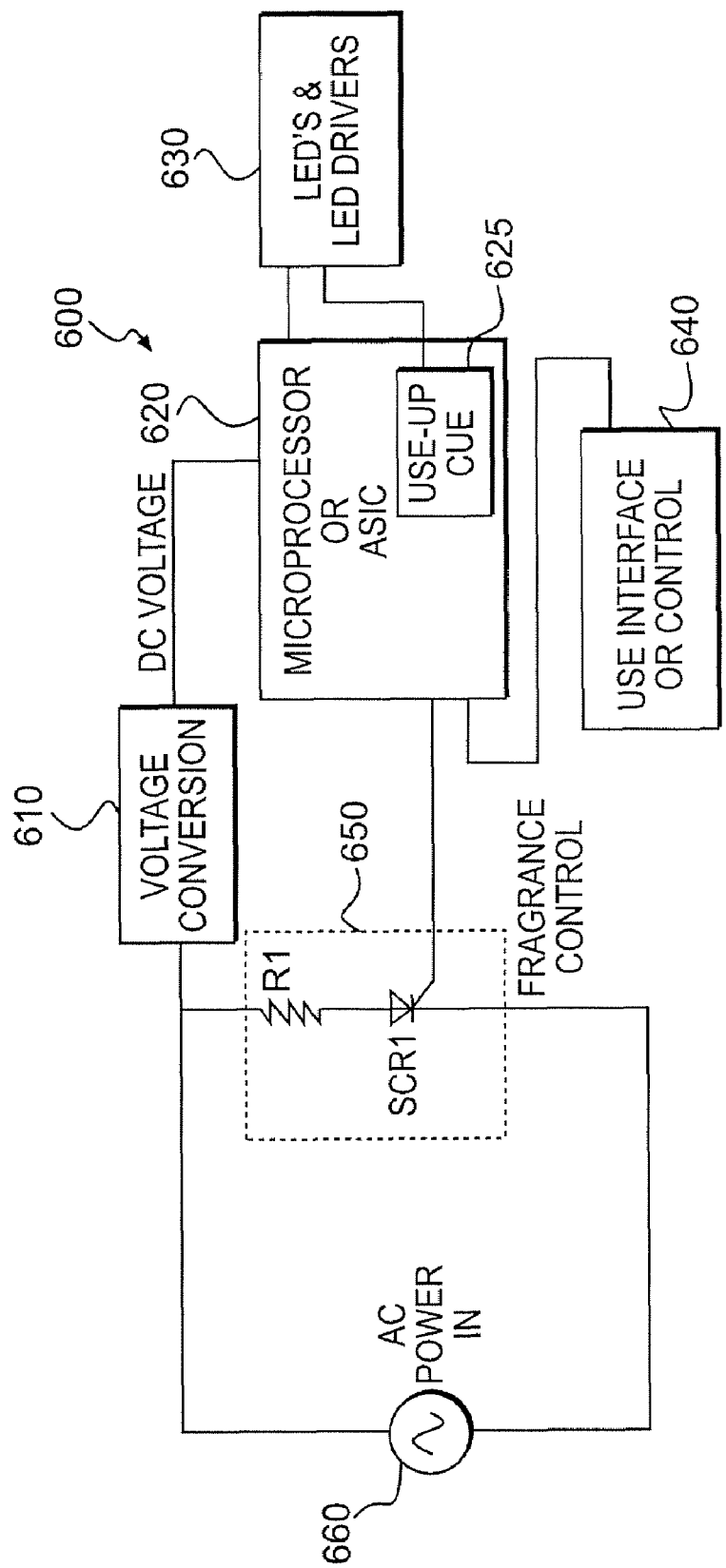
FIG. 12 is a diagram of another circuit for controlling the operation of another embodiment of our invention.

FIG. 12 shows a circuit diagram of yet another control system for operating a device according to our invention. Power is supplied to the system 600 through an AC power source 660. However, battery power could be used in the place of plug-in AC power sources. A voltage conversion device 610 converts the AC voltage from the AC power source 660 to a DC voltage. A microprocessor 620 receives power from voltage conversion device 610 and controls the operation of system 600 using the received power. The microprocessor 620 is controlled by user interface/control 640 (or perhaps a sensor feedback) in any number of ways, including internal programs, user input, etc., as explained in more detail above.

Based on a control program from the user interface/control 640, the microprocessor 620 sends a program signal to LED drivers 630. The LED drivers 630, in turn, control a plurality of LEDs to produce a light show, as also discussed in more detail above. The microprocessor 620 also sends a control signal to fragrance control 650. In this embodiment, the fragrance dispenser being controlled is an evaporative-type dispenser. A resistor R1 is heated by a current passing across the resistor R1. Typically, the resistor R1 is placed adjacent an area at which a fragrance-containing gel or oil is exposed to air and the heat from the resistor R1 causes the fragrance to be vaporized. A switch SCR1 varies the current passing across the resistor R1, thus varying the heat produced by resistor R1 and the rate of vaporization of the fragrance. In alternative embodiments, the resistor R1 may be replaced by a fan which is controlled by switch SCR1, or an atomization device. Also, switch SCR1 may be replaced by an FET in other embodiments.

Microprocessor 620 may also control a use-up cue 625. The use-up cue 625 tracks the use of fragrance control 650 to estimate the time at which the fragrance in the fragrance dispenser is likely to be used up. When the use-up cue 625 determines that fragrance has been spent, it sends a signal to LED drivers 630 to cause the LEDs to illuminate in a pattern, color, or other manner to indicate to a user that it is time to refill or replace a fragrance in the fragrance dispenser.

Again, however, FIG. 12 shows only one possible arrangement for configuring and controlling a device according to our invention. In addition, separate from the specifics of the method for providing control of the system, a plurality of fragrance dispensers may be provided, as well as an audio system. The control logic of a processor used to control a device according to our invention may be suitably modified to account for and control these additional devices, as necessary.

Many different embodiments may be constructed without departing from the spirit and scope of our invention. It should be understood that our invention is not limited to the specific embodiments described in this specification. To the contrary, our invention is intended to cover various modifications and equivalent arrangements included within the spirit and scope of our invention as defined by the claims. The scope of the claims is to be accorded the broadest interpretation so as to encompass all such modifications, equivalent structures and functions.

INDUSTRIAL APPLICABILITY

This invention makes possible an area condition control arrangement wherein the area can be provided with light, fragrance, and/or light in a coordinated manner, thereby to achieve an overall desired effect in the condition of the area.

We claim:

1. An apparatus for producing a combined presentation of light and aroma to produce a desired overall sensory effect, the apparatus comprising:
   a fragrance dispenser for dispensing fragrance, the fragrance dispenser having a fragrance controller for adjusting the rate at which the fragrance dispenser dispenses the fragrance;
   a light source for emitting light show, the light source comprising at least one LED and a light controller for controlling the operation of the at least one LED, and
   a processor for controlling the operation of the light controller and fragrance controller to control the light source and the fragrance dispenser to produce a predetermined presentation for a set period of time, wherein the predetermined presentation sets the rate at which the fragrance dispenser dispenses fragrance over the course of the presentation, and varies at least one of the color and intensity of the at least one LED over the course of the presentation.

2. The apparatus according to claim 1, wherein the fragrance controller and the light controller communicate so as to work in synchronization with each other.

3. The apparatus according to claim 1, wherein the fragrance dispenser dispenses fragrance using a heat-assisted evaporation device.

4. The apparatus according to claim 1, wherein the fragrance dispenser dispenses fragrance using a fan-assisted evaporation device.

5. The apparatus according to claim 1, further comprising a single on/off power switch for operating the fragrance dispenser and the light source.

6. The apparatus according to claim 1, wherein the predetermined presentation varies the rate at which the fragrance dispenser dispenses fragrance over the course of the presentation.

7. The apparatus according to claim 2, wherein the processor is a programable processor that allows a user to program the operation of the fragrance controller and light controller to control both the light source and the fragrance dispenser to produce a desired presentation over a set period.

8. The apparatus according to claim 7, wherein the user may program the processor to set (i) the rate at which the fragrance dispenser dispenses fragrance over the course of the presentation, (ii) and at least one of the color and intensity of the at least one LED.

9. The apparatus according to claim 1, wherein the processor is a programmable processor that allows a user to program the operation of the fragrance controller and light controller to control both the light source and the fragrance dispenser to produce a desired presentation over a set period of time.

10. The apparatus according to claim 9, wherein the user may program the processor to create a presentation that varies at least one of (i) the rate at which the fragrance dispenser dispenses fragrance over the course of the preset presentation, and (ii) at least one of the color and intensity of the at least one LED over the course of the present presentation.

11. The apparatus according to claim 1, further comprising a photosensor which detects light, wherein the photosensor controls at least one of the fragrance controller and light controller to activate the fragrance dispenser and light source, respectively, based on a detection by the photosensor of a predetermined amount of light.

12. The apparatus according to claim 1, further comprising a photosensor which detects light, wherein a detection by the photosensor of a predetermined amount of light causes the processor to produce the predetermined presentation.

13. The apparatus according to claim 1, further comprising a motion sensor which detects motion, wherein the motion sensor controls at least one of the fragrance controller and light controller to activate the fragrance dispenser and light source, respectively, based on a detection by the motion sensor of a predetermined amount of motion.

14. The apparatus according to claim 1, further comprising a timing mechanism for measuring time, wherein a user may program the timing mechanism to cause the processor to begin the predetermined presentation at a set time.

15. The apparatus according to claim 1, further comprising an acoustical generator for generating sounds.

16. The apparatus according to claim 15, further comprising (i) a memory for storing at least one audio file and (ii) a processor for causing the acoustical generator to generate sounds in accordance with the at least one audio file.

17. The apparatus according to claim 16, wherein the processor is programmable so as to allow a user to set control of the acoustical generator, light controller, and fragrance controller to produce a desired presentation over a set period of time, wherein the desired presentation sets at least two of (i) the rate at which the fragrance dispenser dispenses fragrance over the course of the presentation, (ii) at least one of the color and intensity of the at least one LED, and (iii) the audio file played by the acoustical generator.

18. The apparatus according to claim 1, further comprising at least one of a sound sensor for sensing sound levels, a motion sensor for sensing objects moving relative to the apparatus, and a fragrance sensor for sensing fragrance levels in the air,
wherein the at least one sensor controls at least one of the fragrance controller and light controller to activate the fragrance dispenser and light source, respectively.

19. The apparatus according to claim1, wherein said controller is wirelessly connected to the at least one LED or the fragrance controller is wirelessly connected to the fragrance dispenser.

20. An apparatus for producing a combined presentation of light and aroma to produce a desired overall sensory effect, comprising:
a fragrance dispenser for dispensing fragrance, wherein the fragrance dispenser is controllable so as to adjust the rate at which the fragrance dispenser dispenses the fragrance;
a light source for emitting light show, the light source comprising a plurality of LEDs of at least two different colors and being controllable so as to adjust the operation of the plurality of LEDs;
a microprocessor for controlling the rate at which the fragrance dispenser dispenses fragrance and the operation of the light source; and
a master/slave switch operatively connected to the microprocessor to switch the apparatus between a slave mode in which the microprocessor receives signals to control the rate at which the fragrance dispenser dispenses fragrance and the operation of the light source and a master mode in which an internal program generates and the microprocessor transmits the signal.

21. The apparatus according to claim 20, wherein the fragrance dispenser dispenses fragrance using a piezoelectrically actuated atomization device.

22. The apparatus according to claim 20, wherein the fragrance dispenser dispenses fragrance using a heat-assisted evaporation device.

23. The apparatus according to claim 20, wherein the fragrance dispenser dispenses fragrance using a fan-assisted evaporation device.

24. The apparatus according to claim 20, wherein the predetermined presentation sets (i) the rate at which the fragrance dispenser dispenses fragrance over the course of the presentation, and (ii) at least one of the color and intensity of at least one of the plurality of LEDs.

25. The apparatus according to claim 20, wherein the predetermined presentation varies, over the course of the presentation, at least one of (i) the rate at which the fragrance dispenser dispenses fragrance, (ii) the color of at least one of the plurality of LEDs, and (iii) the intensity of at least one of the plurality of LEDS. and (iii) the intensity of at least one of the plurality of LEDs.

26. The apparatus according to claim 20, wherein the microprocessor is programable so as to allow a user to program the operation of both the light source and the fragrance dispenser to produce a desired presentation over a set period of time.

27. The apparatus according to claim 26, wherein the user may program the presentation to set at least one of (i) the rate at which the fragrance dispenser dispenses fragrance over the course of the presentation, (ii) the color of at least one of the plurality of LEDs, and (iii) the intensity of at least one of the plurality of LEDs.

28. The apparatus according to claim 26, wherein the user may program the presentation to vary, over the course of the presentation, at least one of (i) the rate at which the fragrance dispenser dispenses fragrance, (ii) the color of at least one of the plurality of LEDs, and (iii) the intensity of at least one of the plurality of LEDs.

29. The apparatus according to claim 20, further comprising a photosensor for detecting light, wherein the photosensor controls the microprocessor to activate at least one of the fragrance dispenser and light source when the photosensor detects a predetermined amount of light.

30. The apparatus according to claim 24, further comprising a photosensor for detecting light, wherein the photosensor controls the microprocessor to activate the program stored in the memory when the photosensor detects a predetermined amount of light.

31. The apparatus according to claim 20, further comprising a motion sensor which detects motion, wherein the motion sensor controls the microprocessor to activate one of at least one of the fragrance dispenser and light source, based on a detection by the motion sensor of a predetermined amount of motion.

32. The apparatus according to claim 20, further comprising an acoustical generator for generating sounds.

33. The apparatus according to claim 32, further comprising a memory for storing one or more audio files, wherein the microprocessor causes the acoustical generator to generate sounds in accordance with the one or more audio files.

34. The apparatus according to claim 33, wherein the microprocessor allows a user to program the operation of the acoustical generator, light source, and fragrance dispenser to produce a desired presentation.

35. The apparatus according to claim 34, wherein the user may program the presentation to set at least two of (i) the rate at which the fragrance dispenser dispenses fragrance over the course of the presentation, (ii) at least one of the color and intensity of at least one of the plurality of LEDs, and (iii) an audio file to be played by the acoustical generator.

36. The apparatus according to claim 20, further comprising at least one of a sound sensor for sensing sound levels, a motion sensor for sensing objects moving relative to the apparatus, and a fragrance sensor for sensing fragrance levels in the air, wherein the at least one sensor controls the microprocessor to activate the program stored in the memory.

37. An apparatus for producing a combined presentation of light and aroma to produce a desired overall sensory effect, comprising:

a plurality of fragrance dispensers for dispensing fragrance, wherein the fragrance dispensers are separately controllable so as to adjust the rate at which each the fragrance dispenser dispenses fragrance, wherein each of the fragrance dispensers includes a receiver for receiving control signals;

a light source for emitting light show, the light source comprising at least one LED and being controllable so as to adjust the operation of the at least one LED, wherein the light source includes a receiver for receiving control signals; and a microprocessor operatively connected to a transmitter that sends signals to the receivers of the fragrance dispensers and the light source for controlling the rate at which each fragrance dispenser dispenses the fragrance and the operation of the light source.

38. The apparatus according to claim 37, wherein the fragrance dispenser dispenses fragrance using a piezoelectrically actuated atomization device.

39. The apparatus according to claim 37, wherein the fragrance dispensers dispense fragrance using a heat-assisted evaporation device.

40. The apparatus according to claim 37, wherein the fragrance dispensers dispense fragrance using a fan-assisted evaporation device.

41. The apparatus according to claim 37, further comprising a memory, wherein the memory stores a program for causing the microprocessor to control the light source and the plurality of fragrance dispensers to produce a predetermined presentation.

42. The apparatus according to claim 41, wherein the predetermined presentation sets (i) at least one designated fragrance dispenser of the plurality of fragrance dispensers to dispense fragrance, (ii) the rate at which the at least one designated fragrance dispenser dispenses fragrance over the course of the presentation, and (iii) at least one of the color and intensity of the at least one LED.

43. The apparatus according to claim 42, wherein the predetermined presentation varies, over the course of the presentation, at least one of (i) the rate at which the at least one designated fragrance dispenser dispenses fragrance, (ii) which fragrance dispensers are designated to dispense fragrance, (iii) the color of the at least one LED, and (iv) the intensity of the at least one LED.

44. The apparatus according to claim 37, wherein the microprocessor is programable so as to allow a user to program the operation of both the light source and the plurality of fragrance dispensers to produce a desired presentation over a set period of time.

45. The apparatus according to claim 44, wherein the presentation sets at least one of (i) at least one designated fragrance dispenser of the plurality of fragrance dispensers to dispense fragrance over the course of the presentation, (ii) the rate at which at least one designated fragrance dispenser dispenses fragrance over the course of the presentation, (iii) the color of the at least one LED, and (iv) the intensity of at least one LED.

46. The apparatus according to claim 45, wherein the user may program the presentation to vary, over the course of the presentation, at least one of (i) which fragrance dispensers are designated to dispense fragrance, (ii) the rate at which the at least one designated fragrance dispenser dispenses fragrance, (iii) the color of the at least one LED, and (iv) the intensity of the at least one LED.

* * * * *

UNITED STATES PATENT AND TRADEMARK OFFICE
CERTIFICATE OF CORRECTION

PATENT NO.        : 7,687,744 B2
APPLICATION NO.   : 10/514295
DATED             : March 30, 2010
INVENTOR(S)       : Scott D. Walter It is certified that error appears in the above-identified patent and that said Letters Patent is hereby corrected as shown below:

Column 19, Line 32: replace "(ii) a" with --(ii) the--

Column 19, Line 53: replace "claim1" with --claim 1--

Column 20, Line 30: delete ".and the intensity of at least one of the plurality of LEDs."

Column 20, Line 55: replace "claim 24" with --claim 25--

Column 22, Line 37: replace "of at" with --of the at--

Signed and Sealed this

Second Day of November, 2010

David J. Kappos
*Director of the United States Patent and Trademark Office*